United States Patent [19]

Ramuz

[11] 4,355,033

[45] Oct. 19, 1982

[54] 2-IMINO-IMIDAZOLIDINE DERIVATIVES

[75] Inventor: Henri Ramuz, Birsfelden, Switzerland

[73] Assignee: Hoffman-La Roche Inc., Nutley, N.J.

[21] Appl. No.: 178,223

[22] Filed: Aug. 14, 1980

Related U.S. Application Data

[62] Division of Ser. No. 958,300, Oct. 24, 1978, Pat. No. 4,244,957.

[30] Foreign Application Priority Data

Nov. 7, 1977 [LU] Luxembourg .......................... 78467
Sep. 15, 1978 [CH] Switzerland ........................ 9668/78

[51] Int. Cl.³ .................. C07D 403/12; C07D 491/04; A61K 31/415; C07D 417/12
[52] U.S. Cl. .................................... 424/256; 424/270; 424/272; 424/273 R; 424/273 P; 546/116; 548/315; 548/316; 548/186; 548/189; 548/182; 548/213; 548/225; 548/228; 548/229; 548/243
[58] Field of Search ............... 548/315, 316, 186, 189, 548/182, 213, 225, 228, 229, 243; 546/116; 424/256, 270, 272, 273 R, 273 P

[56] References Cited

U.S. PATENT DOCUMENTS

| | | |
|---|---|---|
| 3,236,857 | 2/1966 | Zeile et al. . |
| 3,454,301 | 9/1969 | Zeile et al. . |
| 3,740,412 | 6/1973 | Ullman et al. . |
| 3,752,810 | 8/1973 | Stable et al. . |
| 3,773,767 | 11/1973 | Stable et al. . |
| 3,799,942 | 3/1974 | Boocock et al. . |
| 4,142,051 | 2/1979 | Franzmair ............................ 548/315 |

FOREIGN PATENT DOCUMENTS

| | | |
|---|---|---|
| 623305 | 4/1963 | Belgium . |
| 687657 | 3/1967 | Belgium . |
| 721780 | 4/1969 | Belgium . |
| 721781 | 4/1969 | Belgium . |
| 1815788 | 9/1969 | Fed. Rep. of Germany . |
| 1545628 | 6/1970 | Fed. Rep. of Germany . |
| 1670274 | 7/1970 | Fed. Rep. of Germany . |
| 2058826 | 6/1972 | Fed. Rep. of Germany . |
| 2140405 | 2/1973 | Fed. Rep. of Germany . |
| 2457979 | 6/1976 | Fed. Rep. of Germany . |
| 2709720 | 9/1978 | Fed. Rep. of Germany . |
| 2626128 | 12/1979 | Fed. Rep. of Germany . |
| 126907 | 9/1976 | German Democratic Rep. . |
| 6411516 | 4/1965 | Netherlands . |
| 6806606 | 11/1968 | Netherlands . |
| 6806672 | 11/1968 | Netherlands . |
| 1034938 | 7/1966 | United Kingdom . |

*Primary Examiner*—John M. Ford
*Attorney, Agent, or Firm*—Jon S. Saxe; Bernard S. Leon; William G. Isgro

[57] ABSTRACT

2-Imino-imidazolidine derivatives of the formula

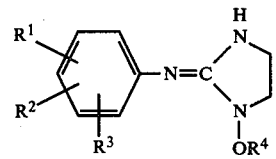

wherein $R^1$, $R^2$, $R^3$ and $R^4$ are as hereinafter set forth, and pharmaceutically acceptable acid addition salts thereof, are described. The 2-imino-imidazolidine derivatives are useful in the treatment of hypertension.

25 Claims, No Drawings

2-IMINO-IMIDAZOLIDINE DERIVATIVES

This is a division, of application Ser. No. 958,300 filed Oct. 24, 1978, now U.S. Pat. No. 4,244,957.

BRIEF SUMMARY OF THE INVENTION

The invention relates to 2-imino-imidazolidine derivatives of the formula

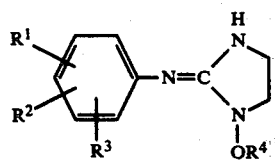

wherein $R^1$, $R^2$ and $R^3$ independently of one another each signify hydrogen, alkyl, alkoxy, alkylthio, halogen, trifluoromethyl, cyano or hydroxy and $R^4$ is hydrogen, alkyl, cycloalkyl, cycloalkenyl, alkenyl, alkynyl, dialkylaminoalkyl, carboxyalkyl, carboxyalkenyl, hydroxyalkyl, cyanoalkyl, arylalkyl, alkylthioalkyl, alkoxycarbonylalkyl, alkoxyalkoxyalkyl, aminocarbonylalkyl, monoalkylaminocarbonylalkyl, dialkylaminocarbonylalkyl, alkoxycarbonylalkenyl, alkoxyalkyl, aminoalkyl, substituted aminoalkyl, aryl, (2,2,8-trimethyl-4H-m-dioxino[4,5-c]pyridin-5-yl)methyl, [5-hydroxy-4-(hydroxymethyl)-6-methyl-3-pyridyl]-methyl, α-carboxybenzyl, α-alkoxycarbonyl-α-alkylphenyl or an aromatic heterocyclic residue with one or two hetero atoms, which is bonded via a —CH($R^5$)-group and is 5-membered which is optionally substituted by alkyl or the group —COOR, or 6-membered which is optionally substituted by alkyl, alkoxy or the group —COOR, possible hetero atoms are oxygen, nitrogen or sulfur, $R^5$ is hydrogen, methyl, ethyl or n-propyl and R is hydrogen or alkyl, and pharmaceutically acceptable acid addition salts thereof.

In another aspect, the invention relates to a process for preparing the compounds of the invention.

DETAILED DESCRIPTION OF THE INVENTION

The invention relates to a 2-imino-imidazolidine derivative of the formula

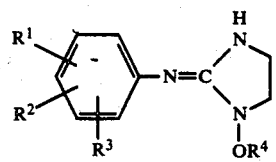

wherein $R^1$, $R^2$ and $R^3$ independently, are hydrogen, alkyl, alkoxy, alkylthio, halogen, trifluoromethyl, cyano or hydroxy and $R^4$ is hydrogen, alkyl, cycloalkyl, cycloalkenyl, alkenyl, alkynyl, dialkylaminoalkyl, carboxyalkyl, carboxyalkenyl, hydroxyalkyl, cyanoalkyl, arylalkyl, alkylthioalkyl, alkoxycarbonylalkyl, alkoxyalkoxyalkyl, aminocarbonylalkyl, monoalkylaminocarbonylalkyl, dialkylaminocarbonylalkyl, alkoxycarbonylalkenyl, alkoxyalkyl, aminoalkyl, substituted aminoalkyl, aryl, (2,2,8-trimethyl-4H-m-dioxino[4,5-c]pyridin-5-yl)methyl, [5-hydroxy-4-(hydroxymethyl)-6-methyl-3-pyridyl]-methyl, α-carboxybenzyl, α-alkoxycarbonyl-α-alkylphenyl or a 5-membered or 6-membered aromatic heterocyclic residue with one or two hetero atoms, which is bonded via a —CH($R^5$)—group, and the 5-membered residue is optionally substituted by alkyl or —COOR and the 6-membered residue is optionally substituted by alkyl, alkoxy or the group —COOR, wherein hetero atoms are oxygen, nitrogen or sulfur, $R^5$ is hydrogen, methyl, ethyl or n-propyl and R is hydrogen or alkyl, or pharmaceutically acceptable acid addition salts thereof.

As used herein, the term "alkyl", alone or in combination, denotes straight-chain and branched alkyl of 1–6 carbon atoms, such as, methyl, ethyl, n-propyl, isopropyl, n-butyl, isobutyl, tert.-butyl, amyl, hexyl, and the like. The term "cycloalkyl" denotes cyclic, saturated hydrocarbon residues of 3–6 carbon atoms, such as cyclopropyl, cyclohexyl, and the like. The term "alkoxy" denotes an alkyl ether group, in which the term "alkyl" is as described above. The term "alkenyl" denotes a straight-chain and branched hydrocarbon of 2–6 carbon atoms, in which at least one carbon-carbon bond is unsaturated, such as, allyl, butenyl, and the like. The term "alkynyl" similarly denotes a straight-chain and branched hydrocarbon of 2–6 carbon atoms, in which at least one carbon-carbon triple bond is present, such as, propargyl, and the like. The term "cycloalkenyl" denotes a cyclic hydrocarbon residue of 3–6 carbon atoms, in which at least one carbon-carbon bond is unsaturated, such as, cyclopropenyl, cyclopentenyl, cyclohexenyl, and the like. The term "halogen" denotes four halogen atoms fluorine, chlorine, bromine and iodine. The term "aryl" denotes a substituted or unsubstituted monocyclic aromatic residue, such as, phenyl, chlorophenyl, tolyl, and the like. The term "substituted amino" denotes a —NH₂ group which is monosubstituted or disubstituted by alkyl. Exemplary of 5-membered or 6-membered aromatic heterocyclic residues with one or two hetero atoms are thienyl, furyl, thiazolyl, oxazolyl, pyrazolyl, imidazolyl, isoxazolyl, isothiazolyl, pyridyl, phthalazinyl, pyrimidinyl and pyrazinyl. As used herein, the term "leaving group" denotes known groups, for example, halogen, preferably chlorine or bromine; arylsulfonyloxy, such as, tosyloxy, or the like; alkylsulfonyloxy, such as, mesyloxy, or the like; quaternary ammonium and sulfonium salts, and the like.

Compounds of formula I which form a preferred class are those wherein $R^3$ is hydrogen. Those compounds of formula I, wherein $R^1$ and $R^2$ are located in the 2,6-position of the phenyl ring are also preferred. $R^1$ and $R^2$ preferably are the same and preferably are halogen, particularly preferable is chlorine.

Compounds of formula I which form yet another preferred class are those wherein $R^4$ is alkynyl, preferably of 3–5 carbon atoms; carboxyalkyl, preferably carboxymethyl or carboxypropyl; alkoxycarbonylalkenyl, preferably ethoxycarbonylalkenyl; or a 5-membered or 6-membered aromatic heterocyclic residue with one or two hetero atoms, which is bonded via a —CH($R^5$)-group and is optionally substituted by alkyl or —COOR, wherein hetero atoms are oxygen, nitrogen or sulfur, $R^5$ is hydrogen, methyl, ethyl or n-propyl and R is hydrogen or alkyl; the heterocyclic residue is preferably pyridyl or an unsubstituted 5-membered aromatic heterocyclic residue with one oxygen or sulfur atom. $R^4$ most preferably is propargyl, carboxymethyl, unbranched ethoxycarbonylalkenyl and pyridyl or furyl bonded via —CH($R^5$)—. $R^5$ preferably is hydrogen or methyl.

From the above, it follows that those compounds of formula I wherein $R^3$ is hydrogen, $R^1$ and $R^2$ are halogen, preferably chlorine, in the 2,6-position, $R^4$ is propargyl, carboxymethyl, unbranched ethoxycarbonylalkenyl or pyridyl or furyl bonded via —CH($R^5$)— and $R^5$ are hydrogen or methyl are most particularly preferred.

The most preferred compounds of formula I are:
2-[(2,6-dichlorophenyl)imino]-1-hydroxyimidazolidine,
2-[(2,6-dibromophenyl)imino]-1-hydroxyimidazolidine,
1-hydroxy-2-[(2-iodophenyl)imino]imidazolidine,
ethyl 4-{[2-[(2,6-dichlorophenyl)imino]-1-imidazolidinyl]oxy}butyrate,
4-{[2-[(2,6-dichlorophenyl)imino]-1-imidazolidinyl]oxy}butyric acid,
ethyl 2-{[2-[(2,6-dichlorophenyl)imino]-1-imidazolidinyl]oxy}butyrate,
2-[(2,6-dichlorophenyl)imino]-1-(2-propynyloxy)-imidazolidine,
{[2-[(2,6-dichlorophenyl)imino]-1-imidazolidinyl]oxy}acetic acid,
ethyl 4-{[2-[(2,6-dichlorophenyl)imino]-1-imidazolidinyl]oxy}crotonate,
2-[(2,6-dichlorophenyl)imino]-1-ethoxyimidazolidine,
1-(2-butynyloxy)-2-[(2,6-dichlorophenyl)imino]imidazolidine,
2-[(2,6-dichlorophenyl)imino]-1-(furfuryloxy)-imidazolidine,
2-{[<2-[(2,6-dichlorophenyl)imino]-1-imidazolidinyl>oxy]methyl}pyridine,
3-{[<2-[(2,6-dichlorophenyl)imino]-1-imidazolidinyl>oxy]methyl}pyridine,
2-{[<-[(2,6-dichloro-4-fluorophenyl)imino]-1-imidazolidinyl>oxy]methyl}pyridine, and
5-{[<2-[(2,6-dichlorophenyl)imino]-1-imidazolidinyl>oxy]methyl}-3-hydroxy-2-methyl-4-pyridinemethanol.

The compounds of formula I and their pharmaceutically acceptable acid addition salts can be prepared in accordance with the invention by a process in which (a) a compound of the formula

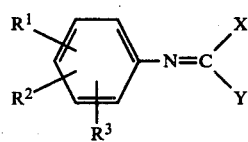

wherein X and Y each are halogen, sulfhydryl, amino, methoxy or alkylthio of 1-3 carbon atoms and $R^1$, $R^2$ and $R^3$ are as previously described, or a compound of the formula

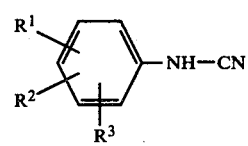

wherein $R^1$, $R^2$ and $R^3$ are as previously described, is reacted with a compound of the formula

wherein $R^4$ is as previously described, or (b) to prepare a compound of formula I wherein $R^4$ is alkyl, cycloalkyl, cycloalkenyl, alkenyl, dialkylaminoalkyl, arylalkyl, alkylthioalkyl, alkoxyalkoxyalkyl, alkoxyalkyl, aryl or a 5-membered or 6-membered aromatic heterocyclic residue with one or two hetero atoms, which is bonded via a —CH($R^5$)-group and is optionally substituted by alkyl, wherein hetero atoms are oxygen, nitrogen or sulfur and $R^5$ is hydrogen, methyl, ethyl or n-propyl, and $R^1$, $R^2$ and $R^3$ are as previously described, a compound of the formula

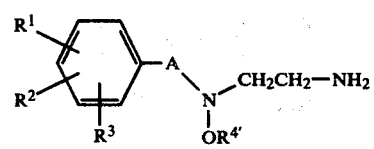

wherein A is $$-N-C- \text{ or } -N=C-$$

and $R^{4'}$ is alkyl, cycloalkyl, cycloalkenyl, alkenyl, dialkylaminoalkyl, arylalkyl, alkylthioalkyl, alkoxyalkoxyalkyl, alkoxyalkyl, aryl or a 5-membered or 6-membered aromatic heterocyclic residue with one or two hetero atoms, which is bonded via a —CH($R^5$)— group and is optionally substituted by alkyl, wherein hetero atoms are oxygen, nitrogen or sulfur and $R^5$ is hydrogen, methyl, ethyl or n-propyl, and $R^1$, $R^2$ and $R^3$ are as previously described, is cyclized, or (c) to prepare a compound of formula I wherein $R^4$ is hydrogen and $R^1$, $R^2$ and $R^3$ are as previously described, the benzyl group in a compound of the formula

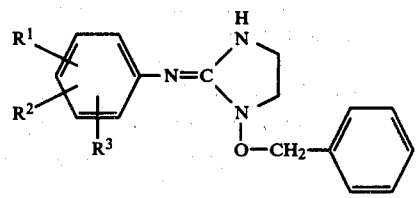

wherein $R^1$, $R^2$ and $R^3$ are as previously described, is split off, or (d) to prepare a compound of the formula

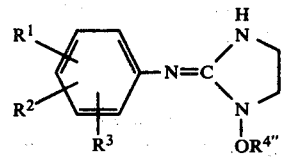

wherein $R^{4''}$ is alkyl, cycloalkyl, cycloalkenyl, alkenyl, alkynyl, dialkylaminoalkyl, carboxyalkyl, hydroxyalkyl, cyanoalkyl, arylalkyl, alkylthioalkyl, alkoxycarbonylalkyl, alkoxyalkoxyalkyl, aminocarbonylalkyl, monoalkylaminocarbonylalkyl, dialkylaminocarbonylalkyl, alkoxycarbonylalkenyl, alkoxyalkyl, aminoalkyl, substituted aminoalkyl, aryl or a 5-membered or 6-membered heterocyclic residue with one or two hetero atoms, which is bonded via a —CH($R^5$)— group and is optionally substituted by alkyl or the group —COOR, wherein hetero atoms are oxygen, nitrogen or sulfur, $R^5$ is hydrogen, methyl, ethyl or n-propyl and R is hydrogen or alkyl, and $R^1$, $R^2$ and $R^3$ are as previously described, a compound of the formula

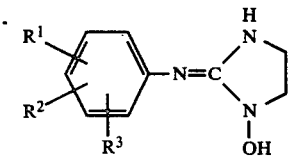

Ic wherein $R^1$, $R^2$ and $R^3$ are as previously described, is reacted with a compound of the formula

R⁴''—X    VI wherein X is a leaving group and $R^{4''}$ is as previously described, or (e) to prepare a compound of formula I wherein $R^4$ is carboxyalkyl or carboxyalkenyl and $R^1$, $R^2$ and $R^3$ are as previously described, a corresponding compound of formula I wherein $R^4$ is alkoxycarbonylalkyl or alkoxycarbonylalkenyl and $R^1$, $R^2$ and $R^3$ are as previously described, is hydrolyzed, or (f) to prepare a compound of formula I wherein $R^4$ is alkoxycarbonylalkyl or alkoxycarbonylalkenyl and $R^1$, $R^2$ and $R^3$ are as previously described, a corresponding compound of formula I wherein $R^4$ is alkoxycarbonylalkyl or alkoxycarbonylalkenyl but in which the alkoxy residue is different, and $R^1$, $R^2$ and $R^3$ are as previously described is trans-esterified with an alkanol, or (g) to prepare a compound of formula I wherein $R^4$ is aminocarbonylalkyl and $R^1$, $R^2$ and $R^3$ are as previously described, a corresponding compound of formula I wherein $R^4$ is alkoxycarbonylalkyl and $R^1$, $R^2$ and $R^3$ are as previously described, is reacted with ammonia, a primary amine or a secondary amine, or (h) to prepare a compound of formula I wherein $R^4$ is hydrogen and $R^1$, $R^2$ and $R^3$ are as previously described, a compound of the formula

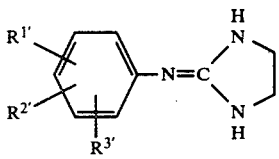

VII wherein $R^{1'}$, $R^{2'}$ and $R^{3'}$, independently, are hydrogen, alkyl, alkoxy, halogen or trifluoromethyl, is oxidized with potassium persulfate in concentrated sulfuric acid, or (i) to prepare a compound of formula I wherein $R^4$ is [5-hydroxy-4-(hydroxymethyl)-6-methyl-3-pyridyl]-methyl and $R^1$, $R^2$ and $R^3$ are as previously described, the ketal group in a compound of the formula

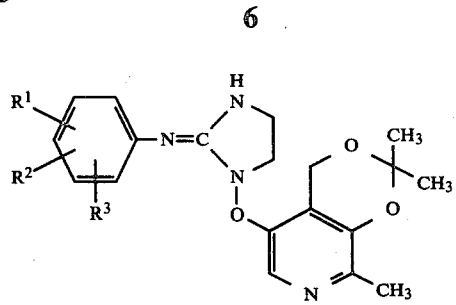

Id wherein $R^1$, $R^2$ and $R^3$ are as previously described, is split off, and (j) if desired, a resulting compound or a pharmaceutically non-acceptable acid addition salt thereof is converted into a pharmaceutically acceptable addition salt thereof.

The reaction of a compound of formula II or III with a compound of formula IV can be carried out in a known manner. The reaction is appropriately effected in an organic solvent which is inert under the reaction conditions, or, for the reaction of a compound of formula II, also in a two-phase system, such as water/toluene, or the like, at a temperature in the range of from about 0° C. to 180° C., which may depend on the residues X and Y. Suitable solvents are non-polar or polar aprotic solvents, or for the reaction of a compound of formula II also polar protic solvents, in any case depending on the residues X and Y, for example, ethers, such as, diethyl ether, tetrahydrofuran, dioxane, or the like; aromatic hydrocarbons, such as, benzene, toluene, xylene, or the like; halogenated hydrocarbons, such as, methylene chloride, chloroform, or the like; esters of alkanoic acids, such as, ethyl acetate, or the like; alcohols, such as, tert.-butanol, amyl alcohol, or the like; acetonitrile, and the like. If one of the residues X and Y is halogen, the reaction is preferably carried out in the presence of an acid-binding agent, such as, triethylamine, N-ethyl-N,N-diisopropylamine, pyridine, a carbonate or the like. The reaction time depends on the reactivity of the starting substances employed and is in the range of a few minutes and several hours.

The cyclization of a compound of formula V is likewise carried out in a known manner, for example, by warming to temperatures in the range of from about 25° to 200° C., preferably in the range of from about 35° to 120° C. The reaction can be carried out in the absence or presence of a solvent. Suitable solvents for this purpose are chlorinated hydrocarbons, such as methylene chloride; ethers, such as tetrahyrofuran; aromatic hydrocarbons, such as toluene; acetonitrile; dimethylformamide; and the like. The cyclization can also be effected by treating a compound of formula V, preferably one wherein A is the group

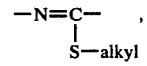

with a suitable basic condensation agent in a polar solvent at a temperature in the range of from about 0° C. to the reflux temperature of the reaction mixture. Suitable basic condensation agents which may be mentioned are ammonium acetate, methylamine, pyridine, or the like. Suitable polar solvents are water, alcohols, such as methanol, and aprotic solvents, such as acetonitrile, or the like.

The benzyl group is split off from a compound of formula Ia by known methods, by treatment with a hydrogen halide acid, preferably hydrobromic acid, or by catalytic hydrogenation. The reaction with a hydrogen halide acid is appropriately carried out in a solvent which is inert under the reaction conditions, preferably water, at a temperature in the range of from about room temperature to 180° C., preferably 100° C. The catalytic hydrogenation is preferably carried out in the presence of a catalyst, such as palladium, palladium-on-charcoal or platinum oxide, in an inert solvent, for example, an alcohol, such as, methanol or ethanol; a carboxylic acid, such as, acetic acid; water; or mixtures thereof, and at a temperature in the range of from about 15° to 50° C. For reasons of expediency, the reaction is preferably carried out at room temperature.

The substitution on the oxygen atom in a compound of the above formula Ic is effected by known methods in the presence of a base, such as sodium hydride, sodium amide, potassium t-butylate, sodium ethylate, thallium ethylate, or the like, in an aprotic polar solvent, such as, dimethylformamide, dimethyl sulfoxide, acetonitrile, or the like, in an aprotic non-polar solvent, for example, ethers, such as, tetrahydrofuran or diethyl ether; aromatic hydrocarbons, such as, toluene or xylene; cyclohexane, or the like; a protic polar solvent, for example, alcohols, such as, t.-butanol or isopropanol; liquid ammonia; or the like. The choice of solvent depends on the base used. Thus, if alcoholates are used, the reaction is carried out in a protic polar or aprotic non-polar solvent, if sodium hydride is used the reaction is carried out in an aprotic polar solvent, and if sodium amide is used the reaction is carried out in an aprotic polar solvent or liquid ammonia. The reaction is effected at a temperature in the range of from about −50° to 100° C., preferably in the range of from about 20° to 45° C., depending on the base used. If thallium ethylate is used as the base, X in the compound of formula VI preferably is iodine. The substitution on the oxygen atom can also be carried out using so-called phase transfer catalysis (PTC) [cf., e.g., Angew. Chem. 89, 521 (1975)]. In this case, the base used is preferably sodium hydroxide or sodium carbonate in a two-phase system, for example, methylene chloride/water, in the presence of a salt, such as, tetrabutylammonium hydrogen sulfate. For reasons of expediency, the reaction is preferably carried out at room temperature.

The ester hydrolysis in accordance with process variant (e) is carried out by known methods, by treatment with an acid or base. Suitable acids and bases for this purpose are sulfuric acid, a hydrogen halide acid, such as hydrochloric acid, or the like; and alkali metal hydroxides, such as, sodium hydroxide or potassium hydroxide, or the like. The hydrolysis is appropriately carried out in an inert solvent. Suitable solvents are alcohols, such as, methanol and ethanol; ethers, such as, dioxane and tetrahydrofuran; dimethylformamide; and the like, in combination with water. The hydrolysis is preferably carried out at a temperature in the range of from about room temperature to the reflux temperature of the reaction mixture.

The trans-esterification in accordance with process variant (f) is also effected in a known manner by reaction with an alcohol, by warming to a temperature in the range of from about 25° to 150° C. The trans-esterification is preferably carried out in the presence of an acid, such as hydrochloric acid, sulfuric acid, or the like. The transesterification is carried out in an inert organic solvent, for example, a hydrocarbon, such as, benzene or toluene; an ether, such as, dioxane or tetrahydrofuran; dimethylformamide; or the like. If the alcohol employed is liquid at the reaction temperature, excess alcohol can also serve as the reaction medium.

The ammonolysis or aminolysis in accordance with process variant (g) is carried out by known methods in the presence or absence of a solvent. Suitable solvents are hydrocarbons, such as, hexane, benzene and toluene; ethers, such as, tetrahydrofuran; alcohols, such as, methanol and ethanol; dimethylformamide, or the like. This reaction is preferably carried out at a temperature in the range of from about 20° to 150° C., preferably in the range of from about 50° to 100° C., under atmospheric pressure or under a pressure above atmospheric pressure.

The oxidation in accordance with process variant (h) is carried out with potassium persulfate in concentrated sulfuric acid at a temperature in the range of from about −10° to 50° C., preferably at room temperature. Since the reaction is highly exothermic, the mixture must be cooled if necessary, so that the reaction temperature does not exceed the upper limit of 50° C.

The ketal splitting in accordance with process variant (i) is carried out by known methods, by treatment with an acid. Suitable acids for this purpose are sulfuric acid; hydrogen halide acids, such as hydrochloric acid; and an organic acid, such as formic acid; or the like. The reaction is appropriately carried out in a solvent. Suitable solvents are alcohols, such as, methanol or ethanol; ethers, such as, dioxane and tetrahydrofuran; water, and the like; or mixtures of the solvents mentioned with water. The splitting of the ketal group is carried out at a temperature in the range of from about 0° to 50° C., preferably at room temperature.

The compounds of formula I can be converted into pharmaceutically acceptable acid addition salts, for instance, by treatment with an inorganic acid, for example, a hydrogen halide acid, such as, hydrochloric acid or hydrobromic acid; sulfuric acid; phosphoric acid; or with an organic acid, such as, oxalic acid, tartaric acid, citric acid, methanesulfonic acid or the like. A pharmaceutically non-acceptable acid addition salt of a compound of formula I can be converted into the free base in a known manner, for example, by treatment with alkali, and, if desired, this base can be converted into a pharmaceutically acceptable acid addition salt.

Some of the compounds of formulas II and III used as the starting material are known and some are novel. The novel compounds can be prepared in a known manner, that is, in a manner analogous to the preparation of the known compounds.

The compounds of formula IV used as starting material are novel and also form part of the invention. They can be prepared, for example, by a process in which an O-aryl- or benzyl-hydroxylamine of the formula

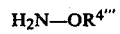    VIII wherein $R^{4'''}$ is aryl or benzyl,
is reacted with a compound of the formula

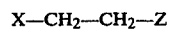    IX wherein Z is phthalimido or succinimido and X is as previously described, or with ethylene imine.

The reaction with a compound of formula IX is effected by known methods in the presence or absence of a solvent at a temperature in the range of from about 50° to 100° C., preferably in the range of from about 80° to 90° C., and yields a compound of the formula $$Z-CH_2CH_2-HN-O-R^{4'''} \qquad Xa$$

wherein $R^{4'''}$ and Z are as previously described. Suitable solvents for this reaction are acetonitrile, tetrahydrofuran, and the like.

A resulting compound of formula Xa wherein $R^{4'''}$ is benzyl can, if desired, be converted into a corresponding compound wherein $R^{4'''}$ has the meaning given for $R^4$, other than benzyl and aryl, by splitting off the benzyl group and, if appropriate, substituting on the oxygen atom. The splitting-off of the benzyl group and, if appropriate, the substitution on the oxygen atom can be carried out under, respectively, the reaction conditions indicated for the reductive splitting-off of the benzyl group from a compound of formula Ia, or in a preferred mode of operation with boron tribromide or boron trichloride in an inert organic solvent, such as, methylene chloride or the like, and under the reaction conditions indicated for the substitution on the oxygen atom in a compound of formula Ic.

The resulting compounds of the formula $$Z-CH_2CH_2-HN-OR^4 \qquad X$$

wherein Z and $R^4$ are as previously described, can be converted by known methods into the corresponding compounds of formula IV, for example, by hydrazinolysis or aminolysis. The reaction can be crried out in the presence of absence of a solvent at a temperature in the range of from about 0° to 40° C., preferably in the range of from about room temperature to 35° C.

In an alternative process, the compound of formula VIII can also be reacted in a known manner with ethylene imine to yield the compound of formula IV wherein $R^4$ is aryl or benzyl. The reaction is appropriately effected in an organic solvent which is inert under the reaction conditions, for example, an aromatic hydrocarbon, such as, benzene, toluene, or the like, in the presence of a weak aprotic Lewis acid, such as, boron trifluoride, or an acid with a weakly nucleophilic anion, such as, tetrafluoroboric acid, perchloric acid, or the like, at a temperature in the range of from about −20° to 50° C., preferably in the range of from about 0° C. to room temperature. A resulting compound of formula IV wherein $R^4$ is benzyl can then, if desired, after conversion into a corresponding compound of formula Xa, be converted as described above into the other compounds of formula IV wherein $R^4$ differs from aryl.

The compounds of formula V used as the starting material are novel and also form part of the invention. They can be prepared, for example, by a process in which an isothiocyanate of the formula

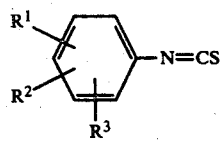

XI wherein $R^1$, $R^2$ and $R^3$ are as previously described, is reacted with a compound of the formula $$R^{4'}O-NH-CH_2CH_2-Z \qquad XII$$

wherein $R^{4'}$ and Z are as previously described, to give a compound of the formula

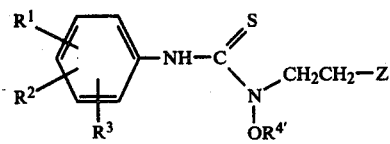

XIII wherein $R^1$, $R^2$, $R^3$, $R^{4'}$ and Z are as previously described. The reaction is effected by known methods in an organic solvent which is inert under the reaction conditions, for example, aromatic hydrocarbons, such as, benzene or toluene; ethers, such as, tetrahydrofuran; alkanols, such as, ethanol; chlorinated hydrocarbons, such as, methylene chloride; or the like. The reaction is effected at a temperature in the range of from about room temperature to the reflux temperature of the reaction mixture.

The compounds of formula XIII can be converted into compounds of the formula

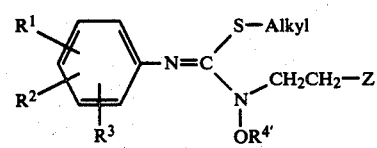

XIV wherein $R^1$, $R^2$, $R^3$, $R^{4'}$ and Z are as previously described, by methods which are also known, for example, by reacting a compound of formula XIII with a trialkyloxonium tetrafluoroborate, such as, triethyloxonium tetrafluoroborate, in an organic solvent, for example, a chlorinated hydrocarbon, such as, methylene chloride; an aromatic hydrocarbon, such as, benzene or toluene, and the like, at a temperature in the range of from about 0° to 40° C., preferably at room temperature.

The compounds of formulas XIII and XIV can be converted into the corresponding compounds of formula V under the conditions indicated for the conversion of a compound of formula X into a compound of formula IV wherein $R^4$ is aryl or benzyl, cyclization sometimes occurs immediately.

The compounds of formulas VI, VII, IX and XI are known or can be prepared in a manner analogous to the preparation of the known compounds.

The compounds of formula XII are novel and also form part of the invention. They can be prepared, for example, from the compounds of formula IV wherein $R^4$ differs from hydrogen, by reacting these compounds with phthalic acid anhydride or succinic acid anhydride in a known manner, in an inert organic solvent, for example, an aromatic hydrocarbon, such as, toluene or xylene; acetonitrile; dimethylformamide, or the like, at a temperature in the range of from about 80° to 150° C., preferably at the reflux temperature of the reaction mixture. This reaction can be catalyzed with a base, such as, triethylamine, or the like. The compounds of formula XII wherein $R^{4'}$ is hydrogen can be prepared from the corresponding compounds of formula XII wherein $R^4$ is benzyl, by splitting off the benzyl group. The benzyl group can be split off under the reaction conditions indicated for reductively splitting off benzyl from the compound of formula Ia, but preferably with boron tribromide or trichloride in an inert organic solvent, such as, methylene chloride and the like.

The compounds of formula I and their pharmaceutically acceptable acid addition salts have valuable cardiovascular activity, in particular valuable hypotensive action, with or without central sympathetic-inhibitory properties, and can accordingly be used for the treatment of hypertension.

the activation of sympathetic influence by more than 30% for more than 30 minutes, it qualifies as "having a central sympathetic-inhibitory action".

The results obtained are summarized in the table which follows. The maximum percentage deviations from the control values and whether or not the compounds have a central sympathetic-inhibitory action is indicated in each case.

| | Spontaneously hypertonic rats | | | Conscious dogs | | | Central sympathetic inhibitory activity |
|---|---|---|---|---|---|---|---|
| Compound | Dose mg/kg, p.o. | Blood pressure Δ % | Heart rate Δ % | Dose mg/kg, p.o. | Blood pressure Δ % | Heart rate Δ % | |
| A | 3 | −14 | −15 | 3 | −19 | −41 | No |
| A | 10 | −26 | −24 | | | | |
| B | 3 | −14 | −5 | 10 | −17 | −47 | No |
| C | 3 | −21 | −20 | 10 | −16 | −6 | No |
| D | 3 | −17 | +9 | 30 | −20 | −36 | No |
| E | 10 (i.p.) | −10 | −17 | 10 | −20 | −7 | No |
| F | 3 | −15 | +5 | 3 | −18 | −23 | No |
| G | 30 | −15 | −54 | 1 | −24 | −9 | Yes |
| H | 3 | −14 | −11 | 10 | −16 | −47 | Yes |
| I | 30 | −19 | −21 | 3 | −20 | −13 | Yes |
| K | 10 | −15 | −19 | 3 | −14 | −37 | Yes |
| L | 3 | −13 | −7 | 1 | −20 | −8 | Yes |
| M | 1 | −13 | −19 | 0.1 | −21 | −13 | Yes |
| | | | | 1 | −32 | −3 | |

The hypotensive action can be determined by the following two methods:

(A) The systolic blood pressure and the heart rate of spontaneously hypertensive conscious female rats are measured several times before administration of the substance. Five test animals with a body weight of about 300 g. are used per dose. The substance is administered by means of a feeding tube. Both parameters are measured 1, 3, 6 and 16 hours after the administration, and the percentage change from the control values is calculated. The systolic blood pressure is measured directly on the tail artery of rats in accordance with the method of Gerold et al. (Helv. Physiol. Acta 24, 58–69, 1966; and Arzneimittelforschung 18, 1285–1287, 1968).

(B) The systolic blood pressure and the heart rate of conscious female dogs which have a body weight of 10–15 kg. are measured before administration of the substance. A modified carotis loop technique in accordance with the method of van Leersum (Pfluger's Arch. ges. Physiol. 142, 377–381, 1911) is used. The substance is administered to animals which have not been fed overnight. Both parameters are measured 0.5, 1, 1.5, 2, 3, 4, 6 and 16 hours after the administration and the percentage change from the control values is calculated. Observation of the test animals, which is carried out simultaneously, is extended 24 hours beyond the time at which the two parameters have reached the control values.

The central sympathetic-inhibitory properties can be determined by the following method:

The action of the test compounds on the activity in the sympathetic nervous system is investigated in cats under urethane anaesthesia. The preganglionic sympathetic activity is derived from the Nervus splanchnicus by means of bipolar platinum electrodes, and the postganglionic sympathetic activity is derived from a branch of a nerve to the kidney, in accordance with the method of G. Häusler (Naunyn-Schmiedeberg's Arch. Pharmacol. 286, 97–111, 1974). The arterial blood pressure from the arteria femoralis and the heart rate are also measured. The test substance is injected intravenously. If a test substance in hypotensive doses inhibits A  2-[(2,6-dichlorophenyl)imino]-1-hydroxyimidazolidine hydrobromide
B  2-[(2,6-dibromophenyl)imino]-1-hydroxyimidazolidine hydrobromide
C  1-hydroxy-2-[(2-iodophenyl)imino]imidazolidine hydrobromide
D  ethyl 4-{[2-[(2,6-dichlorophenyl)imino]-1-imidazolidine]oxy}butyrate hydrochloride
E  4-{[2-[(2,6-dichlorophenyl)imino]-1-imidazolidine]oxy}butyric acid
F  ethyl 2-{[2-[(2,6-dichlorophenyl)imino]-1-imidazolidine]oxy}butyrate hydrochloride
G  2-[(2,6-dichlorophenyl)imino]-1-(2-propynyloxy)imidazolidine hydrochloride
H  {[2-[(2,6-dichlorophenyl)imino]-1-imidazolidine]oxy}acetic acid
I  ethyl 4-{[2-[(2,6-dichlorophenyl)imino]-1-imidazolidine]oxy}crotonate hydrochloide
K  2-[(2,6-dichlorophenyl)imino]-1-ethoxyimidazolidine hydrochloride
L  1-(2-butynyloxy)-2-[(2,6-dichlorophenyl)imino]-imidazolidine hydrochloride
M  2-[(2,6-dichlorophenyl)imino]-1-(furfuryloxy)-imidazolidine hydrochloride The process products and their pharmaceutically acceptable salts can be used as medicaments, for example, in the form of pharmaceutical preparations which contain them or their salts, mixed with a pharmaceutical, organic or inorganic inert carrier material suitable for enteral or parenteral administration, for example, water, gelatin, gum arabic, lactose, starch, magnesium stearate, talc, vegetable oils, polyalkylene glycols, vaseline, and the like. The pharmaceutical preparations can be in the solid form, for example, as tablets, dragees, suppositories or capsules, or in the liquid form, for example, as solutions, suspensions or emulsions. The pharmaceutical preparations are optionally sterilized and/or contain adjuvants, such as preserving, stabilizing, wetting or emulsifying agents, salts for modifying the osmotic pressure or buffers. The pharmaceutical preparations can also additionally contain other therapeutically valuable substances.

The daily dose in the case of oral administration is in the range of from about 1 to 200 mg. and is in the range of from about 0.1 to 20 mg. in the case of intravenous administration. However, the dosages indicated are to be understood as only exemplary and can be altered, depending on the needs of the warm-blooded animal to be treated and at the discretion of the practitioner providing treatment.

The Examples which follow further illustrate the invention. All temperatures are stated in degrees Celsius, unless otherwise mentioned. The melting points are uncorrected.

EXAMPLE 1

Preparation of 1-benzyloxy-2-[(2,6-dichlorophenyl)imino]-imidazolidine

A solution of 36.44 g. of 2,6-dichlorophenylimidocarbonyl chloride is added dropwise to a solution of 24.93 g. of N-(benzyloxy)-ethylene-diamine, 75 ml. of N-ethyl-N,N-diisopropylamine and 300 ml. of absolute ethyl acetate, while stirring, at a rate such that the temperature does not exceed 30°. After the addition has ended, the mixture is further stirred at room temperature overnight. The mixture is extracted five times with water, and the ethyl acetate phase is dried over sodium sulfate. After evaporating off the solvent, the residue is recrystallized from isopropyl ether, whereupon 1-benzyloxy-2-[(2,6-dichlorophenyl)imino]-imidazolidine is obtained, m.p. 115°-117°.

The starting material can be prepared as follows:

(A) A mixture of 12.30 g. of 2-bromoethyl-phthalimide and 12.31 g. of O-benzylhydroxylamine is warmed to 80° for 48 hours. Ethyl acetate is then added, and the precipitate formed is filtered off with suction. The mother liquor is evaporated in vacuo. 35 ml. of methanol are added to the oily residue and the mixture is left to stand at room temperature overnight. The crystalline precipitate is filtered off with suction and dried. The resulting crude product melts at 90°-91°. Analytically pure N-{2-[(benzyloxy)amino]ethyl}phthalimide, m.p. 92°-94°, is obtained by recrystallization from methanol.

(B) A mixture of 50.0 g. of 2-bromoethyl-phthalimide, 100 g. of O-benzylhydroxylamine and 500 ml. of acetonitrile is heated under reflux for 24 hours. A further 100 g. of O-benzylhydroxylamine are then added to the mixture, and the mixture is again heated under reflux for 24 hours. Thereafter, the solvent is evaporated off in vacuo and the excess O-benzylhydroxylamine is distilled off under a high vacuum (0.02 mmHg). The residue is crystallized from methanol, whereupon N-{2-[(benzyloxy)amino]ethyl}phthalimide, m.p. 89°-91°, is obtained. Recrystallization from methanol increases the melting point to 92°-94°.

(C) 26.96 g. of N-{2-[(benzyloxy)amino]ethyl}-phthalimide are suspended in 300 ml. of absolute alcohol, and 40.5 ml. of hydrazine hydrate are added. After stirring the mixture at room temperature for 3 hours, the precipitate formed is filtered off and the mother liquor is evaporated completely. The residue and the precipitate are combined, 600 ml. of 1 N hydrochloric acid are added, and the mixture is stirred vigorously for 3 hours. The precipitate formed is filtered off and dried. The mother liquor is adjusted to pH 9 with 1 N caustic soda solution, and the mixture is saturated with sodium chloride and extracted several times with diethyl ether. After drying over sodium sulfate, the solvent is evaporated off in vacuo. The oily residue is distilled under a high vacuum, whereupon N-(benzyloxy)ethylenediamine, b.p. 110°-115°/0.02 mmHg, is obtained. The corresponding hydrochloride melts at 157°-159° (from methanol/acetonitrile).

(D) 200 ml. of 40% strength methylamine are added to 29.6 g. of N-{2-[(benzyloxy)amino]ethyl}phthalimide and the mixture is stirred at room temperature for 48 hours. The resulting solution is extracted three times with methylene chloride. The organic extracts are evaporated in vacuo and the residue is taken up in ether. The ethereal solution is extracted with 1 M tartaric acid. Ice is added to the acid extracts and the pH is then adjusted to 11 with caustic soda solution. After extracting with ether five times, the organic extracts are dried over sodium sulfate and evaporated to dryness in vacuo, whereupon N-(benzyloxy)ethylenediamine is obtained.

(E) 2.15 g. of aziridine are dissolved in 30 ml. of methylene chloride, and 5.8 ml. of a 9.47 N solution of tetrafluoroboric acid in ether are added at 5°. 6.18 g. of O-benzylhydroxylamine in 40 ml. of methylene chloride are added to this mixture. After 24 hours, the solution is poured onto a 5% strength sodium carbonate solution. The organic phase is washed with a saturated sodium chloride solution, dried and evaporated in vacuo. The residue is purified by distillation under a high vacuum, whereupon N(benzyloxy)ethylenediamine is obtained.

(F) 500 g. of 2,6-dichloroaniline are dissolved in 1000 ml. of formic acid and the solution is heated under reflux for 4 hours. After cooling to 5°, the crystals formed are filtered off and washed with about 1000 ml. of ice-cold isopropanol. 2,6-Dichloroformanilide, m.p. 180°-182°, is obtained. Still further material of the same melting point can be obtained from the mother liquor.

(G) 485 G. of the 2,6-dichloroanilide are added to a mixture of 910 ml. of thionyl chloride and 220 ml. of sulfuryl chloride at a temperature of about 10° in the course of 45 minutes. The solution is then heated under reflux for 9 hours and subsequently left to stand at room temperature overnight. After evaporating off the solvent under reduced pressure, the oily residue is distilled in vacuo, whereupon (2,6-dichlorophenyl)-imidocarbonyl chloride, b.p. 135°-138°/13,5 mmHg, is obtained.

EXAMPLE 2

Preparation of 2-[(2,6-dichlorophenyl)imino]-1-hydroxyimidazolidine hydrobromide A suspension of 45.3 g. of 1-benzoyloxy-2-[(2,6-dichlorophenyl)imino]-imidazolidine in 450 ml. of 48% strength hydrobromic acid is warmed to 80° for 4 hours. The resulting solution is poured onto ice and extracted with ether. The aqueous phase is evaporated in vacuo. The residue is distilled azeotropically five times with a mixture of ethanol/ethyl acetate. 2-[(2,6-dichlorophenyl)imino]-1-hydroxyimidazolidine hydrobromide is obtained by crystallization from a mixture of ethanol/ethyl acetate/ether. An analytically pure sample, m.p. 233°-234°, is obtained by recrystallization from methanol/acetonitrile.

EXAMPLE 3

Preparation of
2-[(2,6-dichlorophenyl)imino]-1-hydroxyimidazolidine 0.6 g. of 2-[(2,6-dichlorophenyl)imino]-1-hydroxyimidazolidine hydrobromide is dissolved in a little water and the pH is adjusted to 10 with 1 N caustic soda solution. The precipitate formed is extracted with methylene chloride. The organic extracts are dried over sodium sulfate and evaporated to dryness. The residue is recrystallized from acetonitrile, whereupon 2-[(2,6-dichlorophenyl)imino]-1-hydroxyimidazolidine, m.p. 215° (decomp.) is obtained.

EXAMPLE 4

Preparation of
2-[(2,6-dichlorophenyl)imino]-1-methoxyimidazolidine 12.5 g. of O-methylhydroxylamine hydrochloride are suspended in 50 ml. of acetonitrile. 12.92 g. of aziridine are added dropwise at 25°. After 1 hour, 75 ml. of N-ethyl-N,N-diisopropylamine are added and the mixture is cooled to 10°. 36 g. of 2,6-(dichlorophenyl)imidocarbonyl chloride are added dropwise, while cooling further, during which the temperature should not exceed 15°. The mixture is then further stirred at room temperature for 4 hours. It is then poured onto water and extracted four times with ether. The organic extracts are dried over sodium sulfate and evaporated in vacuo. The residue is chromatographed on 400 g. of silica gel (eluting agent chloroform/ether 9:1), whereupon 2-[(2,6-dichlorophenyl)imino]-1-methoxyimidazolidine, which, after recrystallization from isopropyl ether, melts at 123°–124°, is obtained.

The base is dissolved in acetonitrile and the pH is adjusted to 1 with hydrogen chloride in dioxane. The resulting hydrochloride melts at 228°–229°.

EXAMPLE 5

Preparation of
1-benzyloxy-2-[(2,6-dichlorophenyl)imino]-imidazolidine 370 mg. of 1-(2-aminoethyl)-1-benzyloxy-3-(2,6-dichlorophenyl)-2-thiourea are heated to 120°. After cooling to room temperature, the residue is crystallized from isopropyl ether, whereupon 1-benzyloxy-2-[(2,6-dichlorophenyl)imino]-imidazolidine, m.p. 115°–117°, is obtained.

The starting material can be prepared as follows:

6.12 g. of 2,6-dichlorophenyl-isothiocyanate are dissolved in 150 ml. of absolute benzene, and 8.89 g. of N-{2-[(benzyloxy)amino]ethyl}phthalimide are added. After 24 hours at room temperature, the crystalline precipitate is filtered off, whereupon 1-benzyloxy-3-(2,6-dichlorophenyl)-1-(2-phthalimidoethyl)-2-thiourea, m.p. 180°–182°, is obtained.

4 g. of 1-benzyloxy-3-(2,6-dichlorophenyl)-1-(2-phthalimidoethyl)-2-thiourea are suspended in 30 ml. of ethanol and 4 ml. of hydrazine hydrate. After approximately 1 hour, a clear solution is formed. The solution is further stirred for 3 hours, whereupon a precipitate forms, which is filtered off. The mother liquor is evaporated in vacuo, and the residue and the precipitate which has been filtered off are suspended in 60 ml. of 1 N hydrochloric acid. After stirring the suspension at room temperature for 16 hours, the precipitate is filtered off and the acid solution is neutralized with 60 ml. of 1 N caustic soda solution. The precipitate thereby formed is filtered off, dried and recrystallized from methanol/isopropyl ether, whereupon 1-(2-aminoethyl)-1-benzyloxy-3-(2,6-dichlorophenyl)-2-thiourea, m.p. 108°–109°, is obtained.

2.0 g. of base are dissolved in 10 ml. of ethyl acetate and the pH is adjusted to 3 with hydrogen chloride in dioxane. The oily suspension is evaporated in vacuo and the residue is recrystallized from acetonitrile. The resulting hydrochloride melts at 170°–171°.

EXAMPLE 6

Preparation of
1-benzyloxy-2-[(2,6-dichlorophenyl)imino]-imidazolidine 200 mg. of 3-(2-aminoethyl)-3-benzyloxy-1-(2,6-dichlorophenyl)-2-ethyl-2-isothiourea are stirred with 20 ml. of methanol and 250 mg. of ammonium acetate at room temperature. The reaction mixture is then evaporated to dryness in vacuo. The residue is dissolved in ethyl acetate, and the organic solution is washed with water, dried over sodium sulfate and evaporated in vacuo. The residue is recrystallized from isopropyl ether, whereupon 1-benzyloxy-2-[(2,6-dichlorophenyl)imino]-imidazolidine, m.p. 117°–118°, is obtained.

The starting material can be prepared as follows:

10.0 g. of 1-benzyloxy-3-(2,6-dichlorophenyl)-1-(2-phthalimidoethyl)-2-thiourea are dissolved in 100 ml. of methylene chloride, and 4.18 g. of triethyloxonium tetrafluoroborate are added. After stirring at room temperature for 3 hours, the solution is poured onto a 5% strength sodium carbonate solution. The organic phase is washed with water, dried over sodium sulfate and evaporated in vacuo. The residue is dissolved in 200 ml. of hot isopropyl ether and the solution is concentrated to 100 ml. 3-Benzyloxy-1-(2,6-dichlorophenyl)-2-ethyl-3-(2-phthalimidoethyl)-2-isothiourea, having a melting point of 102° (decomp.) is obtained.

1.06 g. of 3-benzyloxy-1-(2,6-dichlorophenyl)-2-ethyl-3-(2-phthalimidoethyl)-2-isothiourea are stirred with 6 ml. of 40% strength methylamine at room temperature overnight. The oily suspension is extracted with ether. The organic extracts are washed with water, dried over sodium sulfate and evaporated in vacuo. The residue is dissolved in ether, and hydrogen chloride in dioxane is added. The precipitate which has separated out is filtered off and recrystallized from acetonitrile, whereupon 3-(2-aminoethyl)-3-benzyloxy-1-(2,6-dichlorophenyl)-2-ethyl-2-isothiourea dihydrochloride, m.p. 148° (decomp.) is obtained.

EXAMPLE 7

Preparation of
2-[(2,6-dichlorophenyl)imino]-1-hydroxyimidazolidine 0.34 g. of 1-benzyloxy-2-[(2,6-dichlorophenyl)-imino]imidazolidine is hydrogenated under normal pressure in 5 ml. of ethanol and 2 ml. of 1 N hydrochloric acid in the presence of 0.05 g. of palladium-on-charcoal (5%). After the uptake of hydrogen has ended, the catalyst is filtered off and the solution is evaporated. The residue is dissolved in water and the solution is adjusted to pH 10 with caustic soda solution and extracted, first with methylene chloride and then with ethyl acetate. The organic extracts are dried over sodium sulfate and evaporated to dryness in vacuo. The residue is recrystallized from acetonitrile, whereupon 2-[(2,6-dichlorophenyl)imino]-1-hydroxyimidazolidine, m.p. 196°, is obtained. Recrystallization from methanol-/acetonitrile raises the melting point to 215°.

EXAMPLE 8

Preparation of 2-[(2,6-dichlorophenyl)imino]-1-hydroxyimidazolidine 1.0 g. of 1-benzyloxy-2-[(2,6-dichlorophenyl)imino]imidazolidine is dissolved in 10 ml. of methylene chloride, and 1 ml. of boron tribromide is added carefully at room temperature. After 1 hour, the solution is evaporated in vacuo. The residue is dissolved in water and the solution is adjusted to pH 10 with caustic soda solution and extracted, first with methylene chloride and then with ethyl acetate. The organic extracts are dried over sodium sulfate and evaporated in vacuo. The residue is recrystallized from acetonitrile, whereupon 2-[(2,6-dichlorophenyl)imino]-1-hydroxyimidazolidine, m.p. 211° (decomp.), is obtained.

EXAMPLE 9

Preparation of 2-[(2,6-dichlorophenyl)imino]-1-hydroxyimidazolidine 8.4 g. of 1-benzyloxy-2-[(2,6-dichlorophenyl)imino]imidazolidine in 30 ml. of glacial acetic acid and 2.5 ml. of concentrated sulfuric acid are hydrogenated under normal pressure in the presence of 300 mg. of platinum oxide. After the uptake of hydrogen has ended, the catalyst is filtered off and the filtrate is evaporated. The residue is dissolved in water and the solution is rendered alkaline with sodium carbonate. The precipitate which has formed is filtered off, washed with a little water and dried in vacuo, whereupon 2-[(2,6-dichlorophenyl)imino]-1-hydroxyimidazolidine, m.p. 215°-216°, is obtained.

EXAMPLE 10

Preparation of 1-benzyloxy-2-[(3,4-dimethoxyphenyl)imino]imidazolidine L-tartrate 31.0 g. of 1-benzyloxy-3-(3,4-dimethoxyphenyl)-1-(2-phthalimidoethyl)-2-thiourea are suspended in 600 ml. of ethanol, and 34 ml. of hydrazine hydrate are added. After stirring the mixture at room temperature for 8-12 hours, the mixture is acidified with concentrated hydrochloric acid and stirred at room temperature overnight. The precipitate is filtered off. The aqueous solution is rendered alkaline with sodium carbonate and extracted with ethyl acetate. The organic extract is dried and evaporated in vacuo. The residue is chromatographed on 450 g. of silica gel (eluting agent chloroform/ethyl acetate 3:2). The resulting oil is dissolved in ether, and an excess of L-tartaric acid in ether is added, whereupon 1-benzyloxy-2-[(3,4-dimethoxyphenyl)imino]imidazolidine L-tartrate, m.p. 90°-95°, is obtained.

The starting material can be prepared as follows:

8.20 g. of 3,4-dimethoxyphenyl-isothiocyanate are added to a solution of 12.44 g. of N-[2-(benzyloxy)aminoethyl]phthalimide in 50 ml. of benzene at room temperature. After 36 hours, the precipitate which has formed is filtered off, whereupon 1-benzyloxy-3-(3,4-dimethoxyphenyl)-1-(2-phthalimidoethyl)-2-thiourea, m.p. 120°-122°, is obtained.

EXAMPLE 11

Preparation of 1-benzyloxy-2-[(2,6-dichlorophenyl)imino]imidazolidine 400 ml. of water are added to 143.5 g. of N-(benzyloxy)ethylenediamine dihydrochloride. 207.0 g. of potassium carbonate are gradually added carefully to this suspension. Thereafter, 200 ml. of toluene and then, slowly, 145.7 g. of 2,6-dichlorophenylimidocarbonyl chloride in 100 ml. of toluene are added dropwise in the course of 45 minutes, while stirring vigorously. After 15 minutes, a product begins to separate out. The mixture is further stirred overnight and then poured onto 1 liter of n-hexane. The precipitate is filtered off and washed with water and with n-hexane, whereupon 1-benzyloxy-2-[(2,6-dichlorophenyl)imino]imidazolidine, m.p. 114°-117°, is obtained.

EXAMPLE 12

The following compounds are prepared in an analogous manner to that described in Example 1:

1-benzyloxy-2-[(2,6-dimethylphenyl)imino]imidazolidine hydrobromide of melting point 188°-189° (from acetonitrile/diethyl ether) is obtained from 2,6-dimethylphenylimidocarbonyl chloride and N-(benzyloxy)ethylenediamine;

1-benzyloxy-2-(phenylimino)-imidazolidine of melting point 78°-79° (from isopropyl ether) is obtained from phenylimidocarbonyl chloride and N-(benzyloxy)ethylenediamine;

1-benzyloxy-2-[(2-isopropylphenyl)-imino]imidazolidine is obtained as an oil from 2-isopropylphenylimidocarbonyl chloride and N-(benzyloxy)-ethylenediamine;

1-benzyloxy-2-[(3,4-dichlorophenyl)imino]imidazolidine hydrochloride of melting point 178°-180° (from methanol/acetonitrile) is obtained from 3,4-dichlorophenylimidocarbonyl chloride and N-(benzyloxy)-ethylenediamine;

1-benzyloxy-2-[(6-chloro-2-methylphenyl)imino]imidazolidine hydrochloride of melting point 188°-191° (from acetonitrile) is obtained from 2-chloro-6-methylphenylimidocarbonyl chloride and N-(benzyloxy)ethylenediamine;

1-benzyloxy-2-[(2,6-dibromophenyl)imino]imidazolidine of melting point 89°-90° (from diisopropyl ether/cyclohexane) is obtained from 2,6-dibromophenylimidocarbonyl chloride and N-(benzyloxy)-ethylendiamine;

1-benzyloxy-2-[(4-chloro-2,6-diethylphenyl)imino]imidazolidine is obtained as an oil from 4-chloro-2,6-diethylphenylimidocarbonyl chloride and N-(benzyloxy)ethylenediamine;

1-benzyloxy-2-[(2-iodophenyl)imino]imidazolidine hydrochloride of melting point 192°-194° (from methanol/acetonitrile) is obtained from 2-iodophenylimidocarbonyl chloride and N-(benzyloxy)-ethylenediamine;

1-benzyloxy-2-[(2-chlorophenyl)imino]imidazolidine hydrochloride of melting point 198°-201° (from methanol/acetonitrile/acetone) is obtained from 2-chlorophenylimidocarbonyl chloride and N-(benzyloxy)ethylenediamine;

1-benzyloxy-2-[(2-trifluoromethylphenyl)imino]imidazolidine hydrochloride of melting point 191°-193° (from acetonitrile) is obtained from 2-trifluoromethylphenylimidocarbonyl chloride and N-(benzyloxy)ethylenediamine; and 1-benzyloxy-2-[(2-bromophenyl)imino]imidazolidine hydrochloride of melting point 199°–200° (from acetonitrile) is obtained from 2-bromophenylimidocarbonyl chloride and N-(benzyloxy)-ethylenediamine.

EXAMPLE 13

The following compounds were prepared in an analogous manner to that described in Example 11:

1-benzyloxy-2-[(2-trifluoromethylphenyl)imino]imidazolidine hydrochloride of melting point 191°–193° (from acetonitrile) is obtained from 2-trifluoromethylphenylimidocarbonyl chloride and N-(benzyloxy)ethylenediamine dihydrochloride;

1-benzyloxy-2-[(2-bromophenyl)imino]imidazolidine hydrochloride of melting point 199°–200° (from acetonitrile) is obtained from 2-bromophenylimidocarbonyl chloride and N-(benzyloxy)-ethylenediamine dihydrochloride.

EXAMPLE 14

The following compounds were prepared in an analogous manner to that described in Example 5, paragraph 2 and Example 10, paragraph 2, respectively:

1-benzyloxy-3-(3,4-dimethylphenyl)-1-(2-phthalimidoethyl)-2-thiourea, m.p. 90°–91° (from diethyl ether), is obtained from 3,4-dimethylphenyl-isothiocyanate and N-{2-[(benzyloxy)amino]ethyl}phthalimide;

1-benzyloxy-1-(2-phthalimidoethyl)-3-($\alpha,\alpha,\alpha$-trifluoro-m-tolyl)-2-thiourea, m.p. 123°–124° (from benzene), is obtained from 3-trifluoromethylphenyl-isothiocyanate and N-{2-[(benzyloxy)amino]ethyl}phthalimide; and 1-benzyloxy-3-[4-(methylthio)phenyl]-1-(2-phthalimidoethyl)-2-thiourea is obtained from 4-methylthiophenylisothiocyanate and N-{2-[(benzyloxy)amino]ethyl}phthalimide.

EXAMPLE 15

The following compounds were prepared in an analogous manner to that described in Example 10:

1-benzyloxy-2-[($\alpha,\alpha,\alpha$-trifluoro-m-tolyl)imino]imidazolidine hydrochloride, m.p. 154°–155° (from ethanol/ethyl acetate), is obtained from 1-benzyloxy-1-(2-phthalimidoethyl)-3-($\alpha,\alpha,\alpha$-trifluoro-m-tolyl)-2-thiourea and hydrazine hydrate;

1-benzyloxy-2-{[4-(methylthio)phenyl]imino}imidazolidine, m.p. 96°–97° (from methylene chloride/diisopropyl ether), is obtained from 1-benzyloxy-3-[4-(methylthio)phenyl]-1-(2-phthalimidoethyl)-2-thiourea and hydrazine hydrate; and 1-benzyloxy-2-[(3,4-dimethylphenyl)imino]imidazolidine is obtained from 1-benzyloxy-3-(3,4-dimethylphenyl)-1-(2-phthalimidoethyl)-2-thiourea and hydrazine hydrate.

EXAMPLE 16

The following compounds were prepared in an analogous manner to that described in Example 2:

1-hydroxy-2-[(2,6-dimethylphenyl)imino]imidazolidine hydrobromide, m.p. 177°–179° (from acetone), is obtained from 1-benzyloxy-2-[(2,6-dimethylphenyl)imino]imidazolidine hydrobromide and hydrobromic acid;

1-hydroxy-2-phenylimino)imidazolidine hydrobromide, m.p. 152°–154° (from acetonitrile), is obtained from 1-benzyloxy-2-(phenylimino)imidazolidine and hydrobromic acid;

1-hydroxy-2-[(2-isopropylphenyl)imino]imidazolidine hydrobromide, m.p. 142°–144° (from acetone), is obtained from 1-benzyloxy-2-[(2-isopropylphenyl)imino]imidazolidine and hydrobromic acid;

1-hydroxy-2-[($\alpha,\alpha,\alpha$-trifluoro-m-tolyl)imino]imidazolidine hydrobromide, m.p. 217° with decomposition (from acetonitrile/diethyl ether), is obtained from 1-benzyloxy-2-[($\alpha,\alpha,\alpha$-trifluoro-m-tolyl)imino]imidazolidine and hydrobromic acid;

2-[(3,4-dichlorophenyl)imino]-1-hydroxyimidazolidine hydrobromide, m.p. 204°–206° with decomposition (from methanol/acetonitrile), is obtained from 1-benzyloxy-2-[(3,4-dichlorophenyl)imino]imidazolidine hydrochloride and hydrobromic acid;

1-hydroxy-2-[(3,4-dimethylphenyl)imino]imidazolidine hydrobromide, m.p. 198°–200° (from acetonitrile/diethyl ether), is obtained from 1-benzyloxy-2-[(3,4-dimethylphenyl)imino]imidazolidine and hydrobromic acid;

2-[(6-chloro-2-methylphenyl)imino]-1-hydroxyimidazolidine hydrobromide, m.p. 206°–207° (from acetonitrile), is obtained from 1-benzyloxy-2-[(6-chloro-2-methylphenyl)imino]imidazolidine and hydrobromic acid;

2-[(2,6-dibromophenyl)imino]-1-hydroxyimidazolidine hydrobromide, m.p. 260° (from methanol/acetonitrile), is obtained from 1-benzyloxy-2-[(2,6-dibromophenyl)imino]imidazolidine and hydrobromic acid;

2-[(4-chloro-2,6-diethylphenyl)imino]-1-hydroxyimidazolidine, m.p. 170°–171° (from diisopropyl ether), is obtained from 1-benzyloxy-2-[(4-chloro-2,6-diethylphenyl)imino]imidazolidine and hydrobromic acid;

1-hydroxy-2-[(2-iodophenyl)imino]imidazolidine hydrobromide, m.p. 189°–190° (from acetonitrile), is obtained from 1-benzyloxy-2-[(2-iodophenyl)imino]imidazolidine and hydrobromic acid;

2-[(2-chlorophenyl)imino]-1-hydroxyimidazolidine hydrobromide, m.p. 198°–200° (from methanol/acetonitrile), is obtained from 1-benzyloxy-2-[(2-chlorophenyl)imino]imidazolidine and hydrobromic acid; and 2-[(2-bromophenyl)imino]-1-hydroxyimidazolidine hydrobromide, m.p. 194°–196° (from acetonitrile), is obtained from 1-benzyloxy-2-[(2-bromophenyl)imino]imidazolidine and hydrobromic acid.

EXAMPLE 17

The following compound was prepared in an analogous manner to that described in Example 7:

1-hydroxy-2-[(2-trifluoromethylphenyl)imino]imidazolidine hydrobromide, m.p. 182°–183° (from acetonitrile) is obtained from 1-benzyloxy-2-[(2-trifluoromethylphenyl)imino]imidazolidine and hydrogen in the presence of palladium-on charcoal in ethanolic hydrobromic acid.

EXAMPLE 18

Preparation of
2-[(2,6-dichlorophenyl)imino]-1-methoxyimidazolidine hydrochloride 327 mg. of 2-[(2,6-dichlorophenyl)imino]-1-hydroxyimidazolidine hydrobromide are dissolved in 5 ml. of absolute dimethylformamide, and 90 mg. of sodium hydride are added at 5°. The solution is stirred at room temperature until it becomes clear and is cooled again down to 5° and 1.2 ml. of a 1.0 molar methyl iodide solution in dimethylformamide are added. After 30 minutes, the reaction product is poured onto water and the aqueous phase is extracted twice with ether. The organic extracts are dried and evaporated in vacuo. The residue is dissolved in 1 ml. of acetonitrile, and hydrogen chloride in dioxane is added. The 2-[(2,6-dichlorophenyl)imino]-1-methoxyimidazolidine hydrochloride which has precipitated melts at 228°.

EXAMPLE 19

Preparation of 2-[(2,6-dichlorophenyl)imino]-1-[(2-dimethylamino)ethoxy]imidazolidine 2-[(2,6-dichlorophenyl)imino]-1-[(2-dimethylamino)ethoxy]imidazolidine is prepared from 2-[(2,6-dichlorophenyl)imino]-1-hydroxyimidazolidine hydrobromide and diethylaminoethyl chloride in an analogous manner to Example 18. The corresponding hydrochloride melts at 213°–215° (from acetonitrile/ethyl acetate).

EXAMPLE 20

Preparation of 2-[(2,6-dichlorophenyl)imino]-1-(2-propynyloxy)imidazolidine hydrochloride 1.31 g. of sodium hydride (55% strength suspension) are added to a solution of 6.15 g. of 2-[(2,6-dichlorophenyl)imino]-1-hydroxyimidazolidine in 45 ml. of absolute dimethylformamide at a temperature of 25°. After 30 minutes, 4.16 g. of propargyl bromide are added dropwise. After 30 minutes, the mixture is poured onto 500 ml. of a saturated solution of sodium chloride and the aqueous phase is extracted with ether. The ether extracts are washed with aqueous hydrochloric acid. The aqueous extracts are then rendered basic with 3 N caustic soda solution and extracted with ether. After evaporating off the solvent, the residue is dissolved in ether, and hydrogen chloride in dioxane is added. The residue is recrystallized from methanol/acetonitrile, whereupon 2-[(2,6-dichlorophenyl)imino]-1-(2-propynyloxy)-imidazolidine hydrochloride, m.p. 198°–199° (from methanol/acetonitrile) is obtained.

EXAMPLE 21

The following compounds were prepared in an analogous manner to that described in Example 20:
2-[(2,6-dichlorophenyl)imino]-1-(phenethyloxy)imidazolidine, m.p. 111°–112° (from diisopropyl ether/hexane), is obtained from 2-[(2,6-dichlorophenyl)imino]-1-hydroxyimidazolidine and β-phenethyl bromide. The corresponding hydrochloride, m.p. 167°–169°, was recrystallized from acetone-/ethyl acetate; and
2-[(2,6-dichlorophenyl)imino]-1-[3-(diethylamino)-2,2-dimethylpropoxy]imidazolidine is obtained from 2-[(2,6-dichlorophenyl)imino]-1-hydroxyimidazolidine and 3-(diethylamino)-2,2-dimethylpropyl chloride. The corresponding (R,R)-tartrate (1:1), which crystallizes with 1.1 mol of acid, was crystallized from acetone/ether and melts at 156°–157°.

EXAMPLE 22

Preparation of 2-[(2,6-dichlorophenyl)imino]-1-[2-(methylthio)ethoxy]imidazolidine hydrochloride 6.15 g. of 2-[(2,6-dichlorophenyl)imino]-1-hydroxyimidazolidine in 25 ml. of dimethylformamide and 45 ml. of toluene are stirred with 1.2 g. of sodium amide at room temperature. After one hour, the mixture is warmed at 50° until a clear solution is obtained. Thereafter, the mixture is cooled to room temperature and 3.4 ml. of 2-chloroethylmethyl sulfide are added. The mixture is then warmed to 60° and allowed to react for 16 hours. Thereafter, the reaction mixture is poured onto water and extracted with ether. The ethereal extracts are then extracted with aqueous hydrochloric acid. The aqueous extracts are then rendered basic again with 3 N caustic soda solution and extracted with ether. After drying and evaporating off the solvent, the oily residue is chromatographed on silica gel (eluting agent chloroform/ethyl acetate 9:1). The resulting yellow oil is then dissolved in acetone, and hydrogen chloride in dioxane is added. The precipitate formed is recrystallized from acetone, whereupon 2-[(2,6-dichlorophenyl)imino]-1-[2-(methylthio)ethoxy]imidazolidine hydrochloride, m.p. 156° (decomp.), is obtained.

The following compound was prepared in an analogous manner:
ethyl 4-{[2-[(2,6-dichorophenyl)imino]-1-imidazolidinyl]oxy}butyrate is obtained from 2-[(2,6-dichlorophenyl)imino]-1-hydroxyimidazolidine and 4-bromobutyric acid ethyl ester. The corresponding hydrochloride melts at 113°–115° (from isopropanol-/acetone).

EXAMPLE 23

Preparation of 4-{[2-[(2,6-dichlorophenyl)imino]-1-imidazolidinyl]oxy}-butyric acid 4.80 g. of ethyl 4-{[2-[(2,6-dichlorophenyl)imino]-1-imidazolidinyl]oxy}butyrate are dissolved in 100 ml. of ethanol, 26.6 ml. of 1 N caustic soda solution are added at room temperature and the mixture is left to stand overnight. The solution is then neutralized with 26.6 ml. of 1 N hydrochloric acid and evaporated in vacuo. The dried residue is digested with a hot 1:1:1 mixture of acetonitrile/ethyl acetate/chloroform. The salt is then filtered off from the solution and the filtrate is evaporated in vacuo. The residue is recrystallized from hot acetonitrile, whereupon 4-{[2-[(2,6-dichlorophenyl)imino]-1-imidazolidinyl]oxy}-butyric acid, m.p. 115°–116° (from acetonitrile) is obtained.

EXAMPLE 24

Preparation of 4-{[2-[(2,6-dichlorophenyl)imino]-1-imidazolidinyl]oxy}butyric acid 38.80 g. of ethyl 4-{[2-[(2,6-dichlorophenyl)imino]-1-imidazolidinyl]oxy}-butyrate and 50 ml. of 25% strength hydrochloric acid are warmed to 125° for 45 minutes. The cooled solution is adjusted to pH 5 with sodium acetate and extracted with chloroform. The organic extracts are dried over magnesium sulfate and evaporated in vacuo. The residue is recrystallized from chloroform/ether, whereupon 4-{[2-[(2,6-dichlorophenyl)imino]-1-imidazolidinyl]oxy}butyric acid, m.p. 115°, is obtained.

EXAMPLE 25

The following compound was prepared in an analogous manner to that described in Example 22:

3-{[2-[(2,6-dichlorophenyl)imino]-1-imidazolidinyl]oxy}-1-propanol, m.p. 115°–117° (from methylene chloride/diisopropyl ether) is obtained from 2-[(2,6-dichlorophenyl)imino]-1-hydroxyimidazolidine and 4-[2-(tetrahydropyranyl)oxy]bromopropane. The corresponding hydrochloride melts at 150°–152° (from isopropanol/ethyl acetate).

EXAMPLE 26

Preparation of t-butyl{[2-[(2,6-dichlorophenyl)imino]-1-imidazolidinyl]oxy}phenylacetate t-Butyl{[2-[(2,6-dichlorophenyl)imino]-1-imidazolidinyl]oxy}phenylacetate, m.p. 88°–90° (from cyclohexane), was prepared from 2-[(2,6-dichlorophenyl)imino]-1-hydroxyimidazolidine and α-bromophenylacetic acid t-butyl ester in a manner analogous to that described in Example 20.

EXAMPLE 27

Preparation of {2-[(2,6-dichlorophenyl)imino]-1-imidazolidinyl]oxy}-phenylacetic acid hydrochloride {2-[(2,6-dichlorophenyl)imino]-1-imidazolidinyl]-oxy}phenylacetic acid hydrochloride, m.p. 184°–186° (from chloroform/acetonitrile), is obtained from t-butyl{[2-[(2,6-dichlorophenyl)imino]-1-imidazolidinyl]oxy}phenylacetate in a manner analogous to Example 24, but using 1 N ethanolic hydrochloric acid.

EXAMPLE 28

The following compounds were prepared in a manner analogous to that described in Example 22:

1-(allyloxy)-2-[(2,6-dichlorophenyl)imino]imidazolidine hydrochloride, m.p. 169°–171° (from acetonitrile), is obtained fron 2-[(2,6-dichlorophenyl)imino]-1-hydroxyimidazolidine and allyl bromide;

1-benzyloxy-2-[(2,6-dichlorophenyl)imino]imidazolidine, m.p. 115°–117° (from diisopropyl ether), is obtained from 2-[(2,6-dichlorophenyl)imino]-1-hydroxyimidazolidine and benzyl bromide;

ethyl{[2-[(2,6-dichlorophenyl)imino]-1-imidazolidine]-oxy}acetate hydrochloride, m.p. 171°–173° (from acetonitrile/diethyl ether), is obtained from 2-[(2,6-dichlorophenyl)imino]-1-hydroxyimidazolidine and ethyl bromoacetate;

2-[(2,6-dichlorophenyl)imino]-1-propoxyimidazolidine hydrochloride, m.p. 217°–218° (from methylene chloride/ethyl acetate), is obtained from 2-[(2,6-dichlorophenyl)imino]-1-hydroxyimidazolidine and propyl bromide;

5-{[2-[(2,6-dichlorophenyl)imino]-1-imidazolidinyl]oxy}valeronitrile hydrochloride, m.p. 183°–185° (from acetone/diethyl ether), is obtained from 2-[(2,6-dichlorophenyl)imino]-1-hydroxyimidazolidine and 5-bromovaleronitrile;

2-[(2,6-dichlorophenyl)imino]-1-[2-(2-methoxyethoxy)ethoxy]imidazolidine methanesulfonate (1:1), m.p. 103°–104° (from acetone/diethyl ether), is obtained from 2-[(2,6-dichlorophenyl)imino]-1-hydroxyimidazolidine and β-methoxyethyl β-chloroethyl ether;

1-(3-butenyl)-2-[(2,6-dichlorophenyl)imino]imidazolidine methanesulfonate, m.p. 155°–157° (from acetone/diethyl ether), is obtained from 2-[(2,6-dichlorophenyl)imino]-1-hydroxyimidazolidine and 4-bromo-1-butene;

2-[(2,6-dichlorophenyl)imino]-1-(4-pentenyl)-imidazolidine hydrochloride, m.p. 203°–207° (from acetone), is obtained from 2-[(2,6-dichlorophenyl)imino]-1-hydroxyimidazolidine and 5-bromo-1-pentene;

isopropyl 4-{[2-[(2,6-dichlorophenyl)imino]-1-imidazolidinyl]oxy}butyrate hydrochloride, m.p. 134°–135° (from ethyl acetate), is obtained from 2-[(2,6-dichlorophenyl)imino]-1-hydroxyimidazolidine and bromobutyric acid isopropyl ester;

2-[(2,6-dichlorophenyl)imino]-1-[(3,4-dimethoxyphenethyl)oxy]imidazolidine oxalate (1:1), m.p. 167°–168° (from acetonitrile), is obtained from 2-[(2,6-dichlorophenyl)imino]-1-hydroxyimidazolidine and homoveratryl chloride;

4-{[2-(2,6-dichlorophenyl)imino]-1-imidazolidinyl]oxy}butyronitrile is obtained as an oil from 2-[(2,6-dichlorophenyl)imino]-1-hydroxyimidazolidine and 4-chlorobutyronitrile; the corresponding hydrochloride melts at 183°–184° (from acetonitrile/ethyl acetate);

ethyl 5-{[2-[(2,6-dichlorophenyl)imino]-1-imidazolidinyl]oxy}valerate oxalate (1:1), m.p. 96° (from ethyl acetate), is obtained from 2-[(2,6-dichlorophenyl)imino]-1-hydroxyimidazolidine and 5-bromovaleric acid ethyl ester;

ethyl 4-{[2-(phenylimino)-1-imidazolidinyl]oxy}butyrate is obtained as an oil from 1-hydroxy-2-(phenylimino)imidazolidine and bromobutyric acid ethyl ester;

ethyl 4-{[2-[(6-chloro-2-methylphenyl)imino]-1-imidazolidinyl]oxy}butyrate is obtained as an oil from 2-[(6-chloro-2-methylphenyl)imino]-1-hydroxyimidazolidine and 4-bromobutyric acid ethyl ester;

ethyl 4-{[2-[(2,6-dimethylphenyl)imino]-1-imidazolidinyl]oxy}butyrate is obtained as an oil from 1-hydroxy-2-[(2,6-dimethylphenyl)imino]imidazolidine and 4-bromobutyric acid ethyl ester; and 4-{[2-[(2,6-dichlorophenyl)imino]-1-imidazolidinyl]oxy}1-butanol hydrochloride, m.p. 175°–176° (from methanol/acetonitrile), is obtained from 2-[(2,6-dichlorophenyl)imino]-1-hydroxyimidazolidine and δ-chlorobutyl 2-tetrahydropyranyl ether and subsequent treatment with 3 N hydrochloric acid.

EXAMPLE 29

The following compounds were prepared in an analogous manner to Example 23:

5-{[2-[(2,6-dichlorophenyl)imino]-1-imidazolidinyl]oxy}valeric acid, m.p. 148°–150° (from acetonitrile/ethyl acetate), is obtained from ethyl 5-{[2-[(2,6-dichlorophenyl)imino]-1-imidazolidinyl]oxy}valerate and caustic soda solution;

{2-[(2,6-dichlorophenyl)imino]-1-imidazolidinyl]oxy}acetic acid, m.p. 175°–176° (from acetonitrile), is obtained from ethyl {[2-[(2,6-dichlorophenyl)imino]-1-imidazolidinyl]oxy}acetate and caustic soda solution;

4-{[2-(phenylimino)-1-imidazolidinyl]oxy}butyric acid is obtained as a glassy material from ethyl 4-{[2-(phenylimino)-1-imidazolidinyl]oxy}butyrate and caustic soda solution;

4-{2-[(6-chloro-2-methylphenyl)imino]-1-imidazolidinyl]oxy}butyric acid, m.p. 101°–103° (decomp.) (from acetonitrile), is obtained from ethyl 4-{2-[(6-chloro-2-methylphenyl)imino]-1-imidazolidinyl]oxy}butyrate and caustic soda solution; and 4-{[2-(2,6-dimethylphenyl)-1-imidazolidinyl]oxy}-butyric acid, m.p. 130°–132° (from acetonitrile), is obtained from ethyl 4-{[2-[(2,6-dimethylphenyl)imino]-1-imidazolidinyl]oxy}butyrate and caustic soda solution.

EXAMPLE 30

Preparation of 4-{[2-[(2,6-dichlorophenyl)imino]-1-imidazolidinyl]oxy}butyramide 5.51 g. of ethyl 4-{[2-[(2,6-dichlorophenyl)imino]-1-imidazolidinyl]oxy}butyrate, 200 mg. of sodium methylate and methanolic ammonia are warmed under pressure for 24 hours. The solution is then evaporated in vacuo. The residue is recrystallized from methylene chloride/diethyl ether and then from benzene/cyclohexane (1:1), whereupon 4-{[2-[(2,6-dichlorophenyl)imino]-1-imidazolidinyl]oxy}butyramide, m.p. 140°–141°, is obtained.

EXAMPLE 31

Preparation of methyl 4-{[2-[(2,6-dichlorophenyl)imino]-1-imidazolidinyl]oxy}butyrate 1.0 g. of ethyl 4-{[2-[(2,6-dichlorophenyl)imino]-1-imidazolidinyl]oxy}butyrate is left to stand in 20 ml. of methanolic hydrochloric acid at room temperature overnight. The reaction mixture is then evaporated to dryness with toluene. Sodium carbonate and ether are added to the residue. The organic phase is dried over sodium sulfate and evaporated to dryness. Recrystallization of the residue from cyclohexane gave methyl 4-{[2-[(2,6-dichlorophenyl)imino]-1-imidazolidinyl]oxy}butyrate, m.p. 95°–96°.

EXAMPLE 32

The following compounds were prepared in an analogous manner to that described in Example 22:

ethyl 4-{[2-[(2,6-dichlorophenyl)imino]-1-imidazolidinyl]oxy}crotonate, m.p. 137°–138° (from acetonitrile), is obtained from 2-[(2,6-dichlorophenyl)imino]-1-hydroxyimidazolidine and 4-bromocrotonic acid ethyl ester; the corresponding hydrochloride melts at 139°–140° (from acetone/diethyl ether);

2-[(2-chlorophenyl)imino]-1-(2-propynyloxy)imidazolidine hydrochloride, m.p. 174°–175° (from methanol/acetonitrile), is obtained from 2-[(2-chlorophenyl)imino]-1-hydroxyimidazolidine and propargyl bromide;

ethyl 4-{[2-[(2-chlorophenyl)imino]-1-imidazolidinyl]oxy}butyrate is obtained as an oil from 2-[(2-chlorophenyl)imino]-1-hydroxyimidazolidine and 4-bromobutyric acid ethyl ester;

ethyl 4-{[2-[(2,6-dichlorophenyl)imino]-1-imidazolidinyl]oxy}-2-methylbutyrate is obtained as an oil from 2-[(2,6-dichlorophenyl)imino]-1-hydroxyimidazolidine and 4-bromo-2-methylbutyric acid ethyl ester;

2-[(2,6-dichlorophenyl)imino]-1-isopropoxy-imidazolidine hydrochloride, m.p. 204°–205° (from acetonitrile), is obtained from 2-[(2,6-dichlorophenyl)imino]-1-hydroxyimidazolidine and isopropyl iodide;

2-[(2,6-dichlorophenyl)imino]-1-[(tetrahydrofurfuryl)oxy]imidazolidine hydrochloride, m.p. 172°–173° (from acetone/ethyl acetate), is obtained from 2-[(2,6-dichlorophenyl)imino]-1-hydroxyimidazolidine and tetrahydrofurfuryl bromide;

ethyl 2-{[2-[(2,6-dichlorophenyl)imino]-1-imidazolidinyl]oxy}butyrate hydrochloride, m.p. 176°–177° (from acetonitrile), is obtained from 2-[(2,6-dichlorophenyl)imino]-1-hydroxyimidazolidine and 2-bromobutyric acid ethyl ester;

N-[4-{[2-[(2,6-dichlorophenyl)imino]-1-imidazolidinyl]oxy}butyl]phthalimide, m.p. 125°–126° (from methylene chloride/diisopropyl ether), is obtained from 2-[(2,6-dichlorophenyl)imino]-1-hydroxyimidazolidine and 4-bromobutyl phthalimide;

N-[{[2-[(2,6-dichlorophenyl)imino]-1-imidazolidinyl]oxy}methyl]phthalimide, m.p. 151° (from methylene chloride/disiopropyl ether), is obtained from 2-[(2,6-dichlorophenyl)imino]-1-hydroxyimidazolidine and N-chloromethyl phthalimide;

ethyl 4-{[2-[(2-iodophenyl)imino]-1-imidazolidinyl]oxy}butyrate is obtained as an oil from 1-hydroxy-2-[(2-iodophenyl)imino]imidazolidine and 4-bromobutyric acid ethyl ester;

ethyl 2-{[2-[(2,6-dichlorophenyl)imino]-1-imidazolidinyl]oxy}-2-methylpropionate hydrochloride, m.p. 171°–172° (from ethyl acetate/hydrogen chloride in dioxane/diethyl ether), is obtained from 2-[(2,6-dichlorophenyl)imino]-1-hydroxyimidazolidine and α-bromoisobutyric acid ethyl ester;

N-[2-{[2-[(2,6-dichlorophenyl)imino]-1-imidazolidinyl]oxy}ethyl]phthalimide, m.p. 162°–164° (from isopropyl ether), is obtained from 2-[(2,6-dichlorophenyl)imimo]-1-hydroxyimidazolidine and 2-bromoethyl phthalimide;

2-[(2,6-dichlorophenyl)imino]-1-(3-methoxypropoxy)imidazolidine, m.p. 95°–96° (from isopropyl ether), is obtained from 2-[(2,6-dichlorophenyl)imino]-1-hydroxyimidazolidine and 3-methoxypropyl chloride;

2-[(2,6-dichlorophenyl)imino]-1-ethoxyimidazolidine hydrochloride, m.p. 219°–221° (from acetone), is obtained from 2-[(2,6-dichlorophenyl)imino]-1-hydroxyimidazolidine and ethyl iodide; and 1-(cinnamyloxy)-2-[(2,6-dichlorophenyl)imino]imidazolidine hydrochloride, m.p. 123°–125° (from acetonitrile/hydrogen chloride in dioxane/diethyl ether), is obtained from 2-[(2,6-dichlorophenyl)imino]-1-hydroxyimidazolidine and trans-cinnamyl bromide.

EXAMPLE 33

The following compounds were prepared in an analogous manner to that described in Example 23:

4-{[2-[(2-iodophenyl)imino]-1-imidazolidinyl]oxy}-butyric acid is obtained as a foam from ethyl 4-{[2-[(2-iodophenyl)imino]-1-imidazolidinyl]oxy}butyrate and caustic soda solution;

2-{[2-[(2,6-dichlorophenyl)imino]-1-imidazolidinyl]oxy}butyric acid is obtained as a foam from ethyl 2-{[2-[(2,6-dichlorophenyl)imino]-1-imidazolidinyl]oxy}-butyrate and caustic soda solution;

2-{[2-[(2,6-dichlorophenyl)imino]-1-imidazolidinyl]oxy}-2-methylpropionic acid, m.p. 194°–195° (from chloroform), is obtained from ethyl 2-{[2-[(2,6- dichlorophenyl)imino]-1-imidazolidinyl]oxy}-2-methylpropionate and caustic soda solution;

4-{[2-[(2-chlorophenyl)imino]-1-imidazolidinyl]oxy}-butyric acid is obtained as a foam from ethyl 4-{[2-[(2-chlorophenyl)imino]-1-imidazolidinyl]oxy}butyrate and caustic soda solution;

4-{[2-[(2,6-dichlorophenyl)imino]-1-imidazolidinyl]oxy}-2-methylbutyric acid is obtained from ethyl 4-{[2-[(2,6-dichlorophenyl)imino]-1-imidazolidinyl]oxy}-2-methylbutyrate and caustic soda solution; melting point of the hydrochloride 202°–203° (from acetonitrile); and 2-[{[2-[(2,6-dichlorophenyl)imino]-1-imidazolidinyl]oxy}methyl]-3-furanoic acid, m.p. 175° (decomp.) (from acetonitrile), is obtained from ethyl 2-[{[2-[(2,6-dichlorophenyl)imino]-1-imidazolidinyl]oxy}methyl]-3-furoate and caustic soda solution.

EXAMPLE 34

Preparation of 2-[(2,6-dichlorophenyl)imino]-1-hydroxyimidazolidine 1.2 g. of N-(benzyloxy)ethylenediamine dihydrochloride are warmed to 80° with 20 ml. of 48% strength hydrobromic acid for 3 hours. The warm aqueous solution is then washed rapidly with cyclohexane. N-hydroxyethylenediamine dihydrobromide, m.p. 172° (decomp.), crystallizes from this acidic solution.

2.38 g. of N-hydroxyethylenediamine dihydrobromide, 15 ml. of glacial acetic acid and 5.6 g. of potassium carbonate are warmed on a steambath until the evolution of carbon dioxide has ended. The mixture is then cooled, 2.66 g. of 2,6-dichlorophenylimidocarbonyl chloride are added and the mixture is then warmed intensely on a steambath for 3 minutes and finally left to stand at room temperature for 1 hour. The reaction product is poured onto 100 ml. of water and 40 ml. of 3 N sulfuric acid. The excess 2,6-dichlorophenylimidocarbonyl chloride is extracted with methylene chloride. The aqueous solution is adjusted to pH 6 with concentrated caustic soda solution, and 50 ml. of saturated sodium carbonate solution are then added, whereupon 2-[(2,6-dichlorophenyl)imino]-1-hydroxyimidazolidine of melting point 219°–220° separates out as a crystalline precipitate. The resulting product is identical to the product obtained in Example 3.

EXAMPLE 35

The following compounds are prepared in an analogous manner to Example 11:

1-(benzyloxy)-2-[2,5-dichlorophenyl)imino]-imidazolidine hydrochloride, m.p. 206°–207° (from acetonitrile), is obtained from 2,5-dichlorophenylimidocarbonyl chloride and N-(benzyloxy)ethylenediamine;

1-(benzyloxy)-2-[(2,3-dichlorophenyl)imino]-imidazolidine hydrochloride, m.p. 200°–201° (from acetonitrile/hydrogen chloride in dioxane), is obtained from 2,3-dichlorophenylimidocarbonyl chloride and N-(benzyloxy)ethylenediamine; and 1-(benzyloxy)-2-[(2,4-dichlorophenyl)imino]imidazolidine hydrochloride, m.p. 178°–180° (from acetone/hydrogen chloride in dioxane), is obtained from 2,4-dichlorophenylimidocarbonyl chloride and N-(benzyloxy)ethylenediamine.

EXAMPLE 36

The following compounds were prepared in an analogous manner to Example 2:

2-[(2,5-dichlorophenyl)imino]-1-hydroxyimidazolidine hydrobromide, m.p. 214°–215° (from methanol/acetonitrile), is obtained from 1-(benzyloxy)-2-[(2,5-dichlorophenyl)imino]-imidazolidine;

2-[(2,3-dichlorophenyl)imino]-1-hydroxyimidazolidine hydrobromide, m.p. 190°–191° (from methanol/acetonitrile), is obtained from 1-(benzyloxy)-2-[(2,3-dichlorophenyl)imino]-imidazolidine; and 2-[(2,4-dichlorophenyl)imino]-1-hydroxyimidazolidine hydrobromide, m.p. 217°–218° (from methanol/acetonitrile), is obtraind from 1-(benzyloxy)-2-[(2,4-dichlorophenyl)imino]imidazolidine.

EXAMPLE 37

In an analogous manner to Example 1, paragraph D, 1-(2-aminoethoxy)-2-[(2,6-dichlorophenyl)imino]imidazolidine, m.p. 129°–130° (from acetonitrile), is obtained from N-[2-{[2-[(2,6-dichlorophenyl)imino]-1-imidazolidinyl]oxy}ethyl]phthalimide; the corresponding dihydrochloride melts at 238°–240° (decomp.) (from acetonitrile/diethyl ether);

1-(4-aminobutoxy)-2-[(2,6-dichlorophenyl)imino]imidazlidine is obtained from N-4-[{[2-[(2,6-dichlorophenyl)imino]-1-imidazolidinyl]oxy}butyl]phthalimide; the corresponding dihydrochloride melts at 234°–237° (from acetonitrile/methanol).

EXAMPLE 38

The following compounds were prepared in an analogous manner to that described in Example 20:

1-(2-butynyloxy)-2-[(2,6-dichlorophenyl)imino]imidazolidine hydrochloride, m.p. 198° (decomp.) (from acetonitrile/hydrogen chloride in dioxane), is obtained from 2-[(2,6-dichlorophenyl)imino]-1-hydroxyimidazolidine and 1-bromo-2-butyne, using benzene as the solvent;

2-[(2,6-dichlorophenyl)imino]-1-(furfuryloxy)-imidazolidine, m.p. 123°–124° (from isopropyl ether), is obtained from 2-[(2,6-dichlorophenyl)imino]-1-hydroxyimidazolidine and 2-chloromethylfuran, using toluene as the solvent; the corresponding hydrochloride melts at 162°–164° (from acetonitrile/dioxane/diethyl ether);

ethyl 2-[{[2-[(2,6-dichlorophenyl)imino]-1-imidazolidinyl]oxy}methyl]-3-furoate, m.p. 99° (from isopropyl ether), is obtained from 2-[(2,6-dichlorophenyl)immino]-1-hydroxyimidazolidine and ethyl 2-chloromethyl-3-furoate, using toluene as the solvent; the corresponding fumarate melts at 154°–156° (from methanol/acetonitrile); and 2-[(2,6-dichlorophenyl)imino]-1-(2-thienylmethoxy)-imidazolidine, m.p. 101°–102° (from methylene chloride/cyclohexane), is obtained from 2-[(2,6-dichlorophenyl)-imino]-1-hydroxyimidazolidine and 2-chloromethylthiophene, using toluene as the solvent; the corresponding hydrochloride melts at 211° (decomp.) (from acetone/hydrogen chloride in dioxane).

EXAMPLE 39

In an analogous manner to Example 20, 2-[(2,6-dichlorophenyl)imino]-1-(2-metoxyethoxy)-imidazolidine hydrochloride, m.p. 125°–127° (from acetone/hydrogen chloride in dioxane/diethyl ether), is obtained from 2-[(2,6-dichlorophenyl)imino]-1-hydroxyimidazolidine and β-methoxyethyl chloride; and methyl 4-{[2-(2,6-dichlorophenyl)imino]imidazolidinyl]oxy}-3-methyl crotonate is obtained as a 1:1 cis- trans mixture, m.p. 84°–85° (from isopropyl ether), from 2-[(2,6-dichlorophenyl)imino]-1- hydroxyimidazolidine and 4-bromo-3-methylcrotonic acid methyl ester (cis- trans mixture).

EXAMPLE 40

Preparation of ethyl 2-{[2-[(2,6-dichlorophenyl)imino]-1-imidazolidinyl]oxy}propionate 14.12 g. of tetrabutylammonium hydrogen sulfate, 9.84 g. of 2-[(2,6-dichlorophenyl)imino]-1-hydroxyimidazolidine, 7.97 g. of α-bromopropionic acid ethyl ester and 140 ml. of methylene chloride are stirred at room temperature. 42 ml. of 2.0 N caustic soda solution are slowly poured into this mixture, whereupon a reaction starts immediately. The methylene chloride is distilled off in vacuo and replaced by ether. The ethereal solution is washed with water, dried over magnesium sulfate and evaporated in vacuo. 15 g. of a crystalline product are obtained and are crystallized from cyclohexane, whereupon ethyl 2-{[2-[(2,6-dichlorophenyl)imino]-1-imidazolidinyl]oxy}propionate of melting point 79°–80° is obtained.

The hydrochloride melts at 185°–186° (from acetonitrile/hydrogen chloride in dioxane/diethyl ether).

The following compounds were prepared in an analogous manner:

2-[(2,6-dichlorophenyl)imino]-1-(3-thienylmethoxy)imidazolidine hydrochloride, m.p. 204°–206° (from acetone/hydrogen chloride in dioxane/diethyl ether) is obtained from 2-[(2,6-dichlorophenyl)imino]-1-hydroxyimidazolidine and 3-bromomethylthiophene:

2-[(2,6-dichlorophenyl)imino]-1-[(3-methyl-2-butenyl)-oxy]imidazolidine hydrochloride, m.p. 153°–154° (from acetonitrile/hydrogen chloride in dioxane/diethyl ether) is obtained from 2-[(2,6-dichlorophenyl)imino]-1-hydroxyimidazolidine and 4-bromo-2-methyl-2-butene; and 2-[(2,6-dichlorophenyl)imino]-1-(3-furylmethoxy)-imidazolidine hydrochloride, m.p. 204°–206° (from acetonitrile), is obtained from 2-[(2,6-dichlorophenyl)imino]-1-hydroxyimidazolidine and 3-bromomethylfuran.

EXAMPLE 41

Preparation of 2-[(2,6-dichlorophenyl)imino]-1-hydroxyimidazolidine 2.30 g. of 2-[(2,6-dichlorophenyl)imino]-imidazolidine are dissolved in 10 ml. of concentrated sulfuric acid, and 2.97 g. of potassium persulfate are added in portions at room temperature. The temperature is kept below 50° with a cooling bath. The dark solution is diluted with water and rendered highly alkaline with concentrated caustic soda solution. The unreacted starting material is extracted with ether. The aqueous solution is adjusted to pH 7 with glacial acetic acid and then with sodium bicarbonate. The residue is filtered off from the solution and a potassium carbonate solution is added to the filtrate up to pH 10.5. The product which has precipitated is extracted with ethyl acetate and recrystallized twice from acetonitrile, whereupon 2-[(2,6-dichlorophenyl)imino]-1-hydroxyimidazolidine of melting point 215°, which is identical to the product obtained in Example 3, is obtained.

EXAMPLE 42

Preparation of 2-[(2,6-dichlorophenyl)imino]-1-hydroxyimidazolidine 6.95 g. of hydroxylamine hydrochloride and 13.61 g. of sodium acetate trihydrate are dissolved in 50 ml. of water, and 4.31 g. of aziridine are added (the pH value is 7.61). After 10 minutes, the temperature has risen to 42° and the pH value has dropped to 6.74. The aqueous solution is then evaporated under reduced pressure at 30°. The residue is taken up in glacial acetic acid, and 24.23 g. of (2,6-dichlorophenyl)imidocarbonyl chloride are added, as in Example 34, second paragraph. 2-[(2,6-Dichlorophenyl)imino]-1-hydroxyimidazolidine, m.p. 221°–222° (from acetonitrile), is thus obtained.

EXAMPLE 43

The following compounds were prepared in an analogous manner to that described in Example 30:

4-{[2-(2,6-dichlorophenyl)imino]-1-imidazolidinyl]-oxy}-N-methylbutyramide, m.p. 147°–149° (from methylene chloride/isopropyl ether), is obtained from ethyl 4-{[2-(2,6-dichlorophenyl)imino]-1-imidazolidinyl]oxy}-butyrate and methylamine; and 4-{[2-[(2,6-dichlorophenyl)imino]-1-imidazolidinyl]-oxy}-N,N-dimethylbutyramide, m.p. 126°–128° (from methylene chloride/isopropyl ether), is obtained from ethyl 4-{[2-[(2,6-dichlorophenyl)imino]-1-imidazolidinyl]oxy}butyrate and dimethylamine.

EXAMPLE 44

Preparation of 1-(benzyloxy)-2-[(2,6-dichlorophenyl)imino]imidazolidine 25 ml. of 50% strength tetrafluoroboric acid are added to 24.6 g. of O-benzylhydroxylamine, whereupon the temperature rises to 70°. A solution of 13 ml. of aziridine in 13 ml. of water is added to this solution at 50° at a rate such that the temperature does not exceed 60°. At the end of the exothermic reaction, the mixture is cooled to 5°, and a solution of 56 g. of potassium carbonate in 100 ml. of water is added. 60 ml. of toluene and 35 ml. of (2,6-dichlorophenyl)imidocarbonyl chloride are added, while stirring vigorously. The temperature rises to 43°, carbon dioxide being evolved. The reaction mixture is further stirred for 90 minutes and 150 ml. of hexane and 200 ml. of water are then added. The crystalline mass is washed carefully with water and hexane and dried overnight under reduced pressure. The dried substance is recrystallized from isopropyl ether, whereupon 1-(benzyloxy)-2-[(2,6-dichlorophenyl)imino]imidazolidine, m.p. 115°–117°, is obtained.

EXAMPLE 45

The following compound was prepared in a manner analogous to that described in Example 22:

2-[(2,6-dichlorophenyl)imino]-1-[2-(2-furyl)ethoxy]imidazolidine is obtained as a colorless oil from 2-[(2,6-dichlorophenyl)imino]-1-hydroxyimidazolidine and 2β-chloroethylfuran.

EXAMPLE 46

The following compound was prepared in an analogous manner to that described in Example 40, but toluene was used as the solvent instead of methylene chloride and 28% strength caustic soda solution was used instead of 2 N caustic soda solution:

2-[{[2-[(2,6-dichlorophenyl)imino]-1-imidazolidinyl]oxy}methyl]pyridine, m.p. 116°–118° (from isopropyl ether) is obtained from 2-[(2,6-dichlorophenyl)imino]-1-hydroxyimidazolidine and 2-chloromethylpyridine; the corresponding dihydrochloride melts at 175°–176°, with decomposition (from methanol/acetonitrile).

EXAMPLE 47

The following compound was prepared in an analogous manner to that described in Example 20:

2-[(2,6-dichlorophenyl)imino]-1-(3-pentynyloxy)imidazolidine, m.p. 104°–150° (from isopropyl ether), is obtained from 2-[(2,6-dichlorophenyl)imino]-1-hydroxyimidazolidine and pentyn-3-yl p-toluenesulfonate.

EXAMPLE 48

The following compound was prepared in an analogous manner to that described in Example II:

1-(benzyloxy)-2-[(2,6-dichloro-4-fluorophenyl)imino]imidazolidine, m.p. 112°–113° (from cyclohexane), is obtained from (2,6-dichloro-4-fluorophenyl)imidocarbonyl chloride and 1-(benzyloxy)-2-[(2,6-dichlorophenyl)imino]imidazolidine.

The starting material can be prepared as follows:

97.8 g. of 4-fluoroaniline are dissolved in 600 ml. of glacial acetic acid, and a few drops of concentrated sulfuric acid and then 90 ml. of acetic acid anhydride are slowly added. The solution is warmed on a steambath for 1 hour and cooled to 20°. Thereafter, chlorine gas is passed in for 2 hours, whereupon the temperature rises to 40°. The solution is then warmed to 80° and chlorine gas is passed in for a further 2 hours. The solution is cooled to 20° and 150 ml. of concentrated hydrochloric acid are added. 90 ml. of 30% strength hydrogen peroxide are added dropwise, while cooling, at a rate such that the temperature does not exceed 25°. The solution is warmed to 80° for 1 hour and cooled and the solvent is evaporated off under reduced pressure. Fractional crystallization of the residue gives 2,6-dichloro-4-fluoroacetanilide, m.p. 186°–187° (from ethanol).

19.2 g. of 2,6-dichloro-4-fluoro-acetanilide are heated under reflux in 48% strength hydrobromic acid for 90 minutes. The solution is then cooled and the crystalline precipitate is filtered off, whereupon 2,6-dichloro-4-fluoroaniline hydrobromide, which is employed direct in the next stage, is obtained.

1.3 g. of 2,6-dichloro-4-fluoroaniline hydrobromide are dissolved in 0.5 g. of triethylamine and 3 ml. of formic acid and the solution is heated under reflux for 4 hours. The solution is cooled to −10° and the precipitate which has formed is filtered off, washed with water and dried, whereupon 2,6-dichloro-4-fluoroformanilide, m.p. 165°–168°, is obtained.

1.0 g. of 2,6-dichloro-4-fluoroformanilide is added in portions to a mixture of 1.82 ml. of thionyl chloride and 0.40 ml. of sulfuryl chloride at 10°. The solution is heated under reflux for 10 hours, then left to stand at room temperature for 6 hours and subsequently evaporated under reduced pressure, and the product is then treated with benzene and evaporated again three times. The oily residue is distilled under a high vacuum, whereupon (2,6-dichloro-4-fluorophenyl)imidocarbonyl chloride, b.p. 65°/0.005 mmHg, is obtained.

EXAMPLE 49

The following compound was prepared in an analogous manner to that described in Example 2:

2-[(2,6-dichloro-4-fluorophenyl)imino]-1-hydroxyimidazolidine hydrobromide, m.p. 230°, with decomposition (from 48% strength hydrobromic acid), is obtained from 1-(benzyloxy)-2-[(2,6-dichloro-4-fluorophenyl)imino]imidazolidine and hydrobromic acid.

EXAMPLE 50

The following compounds were prepared in an analogous manner to that described in Example 40:

3-[{[2-(2,6-dichlorophenyl)imino]-1-imidazolidinyl]oxy}methyl]pyridine, m.p. 151°–152° (from methylene chloride/isopropyl ether), is obtained from 2-[(2,6-dichlorophenyl)imino]-1-hydroxyimidazolidine and 3-chloromethylpyridine; the corresponding dihydrochloride melts at 222° with decomposition (from acetonitrile/dioxane);

4-[{[2-[(2,6-dichlorophenyl)imino]-1-imidazolidinyl]oxy}methyl]pyridine, m.p. 160°–161° (from acetonitrile/isopropyl ether), is obtained from 2-[(2,6-dichlorophenyl)imino]-1-hydroxyimidazolidine and 4-chloromethylpyridine; the corresponding dihydrochloride melts at 180° with decomposition (from methanol/acetonitrile);

2-[{[2-[(2,3-dichlorophenyl)imino]-1-imidazolidinyl]oxy}methyl]pyridine dihydrobromide, m.p. 154°–155° with decomposition (from methanol/acetone), is obtained from 2-[(2,3-dichlorophenyl)imino]-1-hydroxyimidazolidine and 2-chloromethylpyridine;

2-[{[2-[(2,4-dichlorophenyl)imino]-1-imidazolidinyl]oxy}methyl]pyridine dihydrochloride, m.p. 179°–180° with decomposition (from acetone), is obtained from 2-[(2,4-dichlorophenyl)imino]-1-hydroxyimidazolidine and 2-chloromethylpyridine;

2-[{[2-[(2,5-dichlorophenyl)imino]-1-imidazolidinyl[oxy}methyl]pyridine is obtained as an oil from 2-[(2,5-dichlorophenyl)imino]-1-hydroxyimidazolidine and 2-chloromethylpyridine;

2-[{[2-[(2,6-dichlorophenyl)imino]-1-imidazolidinyl]oxy}methyl]-5-methylpyridine, m.p. 147°–148° (from methylene chloride/isopropyl ether), is obtained from 2-[(2,6-dichlorophenyl)imino]-1-hydroxyimidazolidine and 2-chloromethyl-5-methylpyridine; the corresponding dihydrobromide melts at 163°–164° with decomposition (from acetonitrile);

2-[{[2-[(2,6-dichlorophenyl)imino]-1-imidazolidinyl]oxy}methyl]-6-methylpyridine, m.p. 132°–133° (from acetone/isopropyl ether), is obtained from 2-[(2,6-dichlorophenyl)imino]-1-hydroxyimidazolidine and 2-chloromethyl-6-methylpyridine; the corresponding dihydrochloride melts at 190° with decomposition (from acetone);

2-[{[2-[(2,6-dichlorophenyl)imino]-1-imidazolidinyl]oxy}methyl]-5-ethylpyridine, m.p. 103°–104° (from isopropyl ether), is obtained from 2-[(2,6-dichlorophenyl)imino]-1-hydroxyimidazolidine and 2-chloromethyl-5-ethylpyridine;

Rac.-2-[1-{[2-[(2,6-dichlorophenyl)imino]-1-imidazolidinyl[oxy}ethyl]pyridine dihydrochloride, m.p. 218°–219° (from acetonitrile/acetone) is obtained from 2-[(2,6-dichlorophenyl)imino]-1-hydroxyimidazolidine and 2-α-chloroethylpyridine;

5-[{[2-[(2,6-dichlorophenyl)imino]-1-imidazolidinyl]oxy}methyl]isoxazole, m.p. 87°–88° (from isopropyl ether), is obtained from 2-[(2,6-dichlorophenyl-)imino]-1-hydroxyimidazolidine and 5-bromomethylisoxazole; the corresponding hydrochloride melts at 171° with decomposition (from acetone);

2-[{[2-[(2-chlorophenyl)imino]-1-imidazolidinyl]oxy}-methyl]pyridine dihydrochloride, m.p. 175°-176° (from acetonitrile/dioxane), is obtained from 2-[(2-chlorophenyl)imino]-1-hydroxyimidazolidine and 2-chloromethylpyridine;

2-[{[2-[(2-bromophenyl)imino]-1-imidazolidinyl]oxy}-methyl]pyridine dihydrobromide, m.p. 186°-187° (from 30% strength hydrobromic acid in glacial acetic acid) is obtained from 2-[(2-bromophenyl-)imino]-1-hydroxyimidazolidine and 2-chloromethylpyridine;

2-[{[2-[(2,6-dibromophenyl)imino]-1-imidazolidinyl]oxy}methyl]pyridine dihydrochloride, m.p. 187°-188° with decomposition (from methanol/acetonitrile), is obtained from 2-[(2,6-dibromophenyl)imino]-1-hydroxyimidazolidine and 2-chloromethylpyridine;

2-[{[2-[(2,6-dimethylphenyl)imino]-1-imidazolidinyl]oxy}methyl]pyridine dihydrochloride, m.p. 196°-197° with decomposition (from acetonitrile), is obtained from 1-hydroxy-2-[(2,6-dimethylphenyl-)imino]imidazolidine and 2-chloromethylpyridine;

2-[{[2-[(6-chloro-2-methylphenyl)imino]-1-imidazolidinyl]oxy}methyl]pyridine dihydrochloride, m.p. 187° (from acetonitrile), is obtained from 2-[(6-chloro-2-methylphenyl)imino]-1-hydroxyimidazolidine and 2-chloromethylpyridine;

3-[{[2-[(6-chloro-2-methyl)imino]-1-imidazolidinyl]oxy}methyl]pyridine, m.p. 110°-111° (from methylene chloride/isopropyl ether), is obtained from 2-[(6-chloro-2-methylphenyl)imino]-1-hydroxyimidazolidine and 3-chloromethylpyridine; the corresponding dihydrochloride melts at 221°-222° with decomposition (from acetonitrile);

2-chloro-6-[{[2-[(2,6-dichlorophenyl)imino]-1-imidazolidinyl]oxy}methyl]pyridine dihydrobromide, m.p. 179°-181° (from methanol/acetone), is obtained from 2-[(2,6-dichlorophenyl)imino]-1-hydroxyimidazolidine and 2-chloromethyl-6-chloropyridine;

2-[{[2-[(2,6-dichloro-4-fluorophenyl)imino]-1-imidazolidinyl]oxy}methyl]pyridine dihydrobromide, m.p. 199°-200° with decomposition (from methanol/acetonitrile), is obtained from 2-[(2,6-dichloro-4-fluorophenyl)imino]-1-hydroxyimidazolidine and 2-chloromethylpyridine;

5-[{[2-[(2,6-dichlorophenyl)imino]-1-imidazolidinyl]oxy}methyl]-2,2,8-trimethyl-4H-m-dioxino[4,5-c]pyridine, m.p. 190°-192° (from methanol/acetonitrile), is obtained from 2-[(2,6-dichlorophenyl)imino]-1-hydroxyimidazolidine and 5-chloromethyl-2,2,8-trimethyl-4H-m-dioxino[4,5-c]pyridine;

4-[1-{[2-[(2,6-dichlorophenyl)imino]-1-imidazolidinyl]oxy}ethyl]pyridine dihydrochloride, m.p. >300° (from methanol/acetonitrile), is obtained from 2-[(2,6-chlorophenyl)imino]-1-hydroxyimidazolidine and 4-α-chloroethylpyridine;

5-[{[2-[(2,6-dichlorophenyl)imino]-1-imidazolidinyl]oxy}methyl]-2,3-dimethoxypyridine dihydrochloride, m.p. 172°-175° with decomposition (from acetonitrile/dioxane), is obtained from 2-[(2,6-dichlorophenyl)imino]-1-hydroxyimidazolidine and 5,6-dimethoxy-3-chloromethylpyridine; and 3-[1-}[2-[(2,6-dichlorophenyl)imino]-1-imidazolidinyl]oxy}ethyl]pyridine dihydrochloride, m.p. 262° with decomposition (from acetonitrile/dioxane), is obtained from 2-[(2,6-dichlorophenyl)imino]-1-hydroxyimidazolidine and 3-α-chloroethylpyridine.

EXAMPLE 51

Preparation of 1-[3-(benzyloxy)propoxy]-2-[(2,6-dichlorophenyl-)imino]imidazolidine 9.84 g. of 2-[(2,6-dichlorophenyl)imino]-1-hydroxyimidazolidine are dissolved in 100 ml. of 40% strength tetrabutylammonium hydroxide, and 10.16 g. of γ-chloropropyl benzyl ether are added. The solution is left to stand overnight and then diluted with water and extracted with ether. The ether extracts are shaken with 1 N sulfuric acid. The aqueous phase is rendered alkaline with ammonia and extracted with ether. The ether extracts are dried over sodium sulfate and evaporated. The oily residue is recrystallized from methylene chloride/isopropyl ether, whereupon 1-[3-(benzyloxy)-propoxy]-2-[(2,6-dichlorophenyl)imino]imidazolidine, m.p. 79°-80°, is obtained.

The following compound was prepared in an analogous manner:

1-(cyclohexyloxy)-2-[(2,6-dichlorophenyl-)imino]imidazolidine fumarate, m.p. 163°-164° (from acetone) is obtained from 2-[(2,6-dichlorophenyl-)imino]-1-hydroxyimidazolidine and cyclohexyl bromide.

EXAMPLE 52

Preparation of 5-[{[2-[(2,6-dichlorophenyl)imino]-1-imidazolidinyl]oxy}methyl]-3-hydroxy-2-methyl-4-pyridinemethanol dihydrochloride 3.7 g. of 5-[{[2-[(2,6-dichlorophenyl)imino]-1-imidazolidinyl]oxy}methyl]-2,2,8-trimethyl-4H-m-dioxino[4,5-c]pyridine are dissolved in 50 ml. of ethanol, 50 ml. of 3 N hydrochloric acid are added at room temperature and the mixture is left to stand for two days. The solution is evaporated and the residue is recrystallized from methanol/acetonitrile, whereupon 5-[{[2-[(2,6-dichlorophenyl)imino]-1-imidazolidinyl]oxy}methyl]-3-hydroxy-2-methyl-4-pyridinemethanol dihydrochloride, m.p. 216°-218°, is obtained.

EXAMPLE A

Preparation of coated tablets of the following composition:

| | |
|---|---|
| 2-[(2,6-dichlorophenyl)imino]-1-(furfuryl-oxy)-imidazolidine hydrochloride | 5.56 mg. |
| Powdered lactose | 34.44 mg. |
| White maize starch | 59.0 mg. |
| Talc | 0.5 mg. |
| Magnesium stearate | 0.5 mg. |
| core weight | 100.0 mg |
| Solids content of coating about | 7.0 mg. |
| coated tablet weight about | 107.0 mg. |

A mixture of 2-[(2,6-dichlorophenyl)imino]-1-(furfuryloxy)imidazolidine hydrochloride with the powdered lactose and some of the maize starch is moistened with a paste of a further portion of the maize starch and water and the mixture is kneaded, granulated, dried and sieved. This granulate is mixed with the rest of the maize starch, the talc and the magnesium stearate and pressed to cores weighing 100 mg. The cores are coated by means of one of the customary methods, with a solids content of the coating of about 7.0 mg.

EXAMPLE B

Preparation of coated tablets of the following composition:

| | |
|---|---|
| ethyl 2-{[2-[(2,6-dichlorophenyl)imino]-1-imidazolidinyl]oxy}butyrate hydrochloride | 11.1 mg. |
| Powdered lactose | 104.9 mg. |
| White maize starch | 125.0 mg. |
| Talc | 9.0 mg. |
| Magnesium stearate | 1.0 mg. |
| core weight | 350.0 mg. |
| Solids content of coating about | 20.0 mg. |
| Coated tablet weight about | 370.0 mg. |

The mixture of ethyl 2-{[2-[(2,6-dichlorophenyl)imino]-1-imidazolidinyl]oxy}-butyrate hydrochloride with the powdered lactose and some of the maize starch is moistened with a paste of a further portion of the maize starch and water and the mixture is kneaded, granulated, dried and sieved. This granulate is mixed with the rest of the maize starch, the talc and the magnesium stearate and pressed to cores weighing 350 mg. The cores are coated by means of one of the customary methods, with a solids content of the coating of about 20 mg.

I claim:

1. A compound of the formula

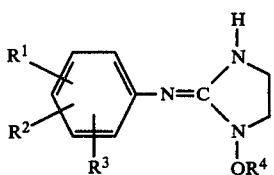

wherein $R^1$, $R^2$ and $R^3$, independently, are hydrogen, alkyl, alkoxy, alkylthio, halogen, trifluoromethyl, cyano or hydroxy and $R^4$ is hydrogen, alkyl, cycloalkyl, cycloalkenyl, alkenyl, alkynyl, carboxyalkyl, carboxyalkenyl, hydroxyalkyl, cyanoalkyl, phenylalkyl, chlorophenylalkyl, tolylalkyl, alkylthioalkyl, alkoxycarbonylalkyl, alkoxyalkoxyalkyl, aminocarbonylalkyl, monoalkylaminocarbonylalkyl, dialkyl-aminocarbonylalkyl, alkoxycarbonylalkenyl, alkoxyalkyl, aminoalkyl, alkylaminoalkyl, dialkylaminoalkyl, phenyl, chlorophenyl, tolyl, (2,2,8-trimethyl-4H-m-dioxino[4,5-c]-pyridin-5-yl)methyl, α-carboxybenzyl, α-alkoxycarbonyl-α-alkylphenyl, or an aromatic heterocyclic residue selected from the group consisting of thienyl, furyl, thiazolyl, oxazolyl, pyrazolyl, imidazolyl, isoxazolyl and isothiazolyl, which is bonded via a —CH($R^5$)— group and is optionally substituted by alkyl or the group —COOR, wherein $R^5$ is hydrogen, methyl, ethyl or n-propyl and R is hydrogen or alkyl, and wherein above, each occurrence, the alkyl, alkoxy and alkylthio groups, independently, are of 1–6 carbon atoms, or a pharmaceutically acceptable acid addition salt thereof.

2. A compound in accordance with claim 1, wherein $R^1$, $R^2$ and $R^3$, independently, are hydrogen, alkyl, alkoxy, alkylthio, halogen, trifluoromethyl, cyano or hydroxy and $R^4$ is hydrogen, alkyl, cycloalkyl, alkenyl, alkynyl, carboxyalkyl, carboxyalkenyl, hydroxyalkyl, cyanoalkyl, phenylalkyl, chlorophenylalkyl, tolylalkyl, alkylthioalkyl, alkoxycarbonylalkyl, alkoxyalkoxyalkyl, aminocarbonylalkyl, alkoxycarbonylalkenyl, alkoxyalkyl, aminoalkyl, alkylaminoalkyl, dialkylaminoalkyl, α-carboxybenzyl, α-alkoxycarbonyl-α-alkylphenyl, or an aromatic heterocyclic residue selected from the group consisting of thienyl, furyl, thiazolyl, oxazolyl, pyrazolyl, imidazolyl, isoxazolyl and isothiazolyl, which is bonded via a —CH($R^5$)— group and is optionally substituted by alkyl or the group —COOR, wherein $R^5$ is hydrogen, methyl, ethyl or n-propyl and R is hydrogen or alkyl, and wherein above, each occurrence, the alkyl, alkoxy and alkylthio group; independently, are of 1–6 carbon atoms.

3. A compound in accordance with claim 1 or 2, wherein $R^3$ is hydrogen.

4. A compound in accordance with claim 3, wherein $R^1$ and $R^2$ are located in the 2,6-position of the phenyl ring.

5. A compound in accordance with claim 4, wherein $R^1$ and $R^2$ are the same.

6. A compound in accordance with claim 5, wherein $R^1$ and $R^2$ are halogen.

7. A compound in accordance with claim 6, wherein $R^1$ and $R^2$ are chlorine.

8. A compound in accordance with claim 7, wherein $R^4$ is alkynyl, carboxyalkyl, alkoxycarbonylalkenyl, or an aromatic heterocylic residue selected from the group consisting of thienyl, furyl, thiazolyl, oxazolyl, pyrazolyl, imidazolyl, isoxazolyl or isothiazolyl, which is bonded via a —CH($R^5$)— group and is optionally substituted by alkyl or —COOR, wherein $R^5$ is hydrogen, methyl, ethyl or n-propyl and R is hydrogen or alkyl, and wherein above, each occurrence the alkyl, alkoxy and alkylthio groups, independently, are of 1–6 carbon atoms.

9. A compound in accordance with claim 8, wherein $R^4$ is alkynyl with 3–5 carbon atoms, carboxymethyl, carboxypropyl, ethoxycarbonylalkenyl, or an aromatic heterocyclic residue selected from the group consisting of thienyl and furyl, which is bonded via a —CH($R^5$)— group, wherein $R^5$ is hydrogen or methyl.

10. A compound in accordance with claim 9, wherein $R^4$ is propargyl, carboxymethyl, unbranched ethoxycarbonylalkenyl or furyl bonded via a —CH($R^5$)— group.

11. A compound in accordance with claim 1 or 2, wherein $R^3$ is hydrogen, $R^1$ and $R^2$ are halogen, in the 2,6-position, $R^4$ is propargyl, carboxymethyl, unbranched ethoxycarbonylalkenyl or furyl bonded via a —CH($R^5$)— group and $R^5$ is hydrogen or methyl.

12. A compound in accordance with claim 1, 2-[(2,6-dichlorophenyl(imino]-1-hydroxyimidazolidine.

13. A compound in accordance with claim 1, 2-[(2,6-dibromophenyl)imino]-1-hydroxyimidazolidine.

14. A compound in accordance with claim 1, 1-hydroxy-2-[(2-iodophenyl)-imino]imidazolidine.

15. A compound in accordance with claim 1, ethyl 4-{[2-[(2,6-dichlorophenyl)-imino]-1-imidazolidinyl]oxy}butyrate.

16. A compound in accordance with claim 1, 4-{[2-[(2,6-dichlorophenyl)imino]-1-imidazolidinyl]oxy}-butyric acid.

17. A compound in accordance with claim 1, ethyl 2-{[2-[(2,6-dichlorophenyl)-imino]-1-imidazolidinyl]oxy}butyrate.

18. A compound in accordance with claim 1, 2-[(2,6-dichlorophenyl)imino]-1-(2-propynyloxy)imidazolidine.

19. A compound in accordance with claim 1, {[2-[(2,6-dichlorophenyl)imino]-1-imidazolidinyl]oxy}acetic acid.

20. A compound in accordance with claim 1, ethyl 4-{[2-(2,6-dichlorophenyl)-imino]-1-imidazolidinyl]oxy}crotonate.

21. A compound in accordance with claim 1, 2-[(2,6-dichlorophenyl)imino]-1-ethoxyimidazolidine.

22. A compound in accordance with claim 1, 1-(2-butynyloxy)-2-[(2,6-dichlorophenyl)imino]imidazolidine.

23. A compound in accordance with claim 1, 2-[(2,6-dichlorophenyl)imino]-1-(furfuryloxy)imidazolidine.

24. A composition for the treatment of hypertension which comprises a compound of the formula

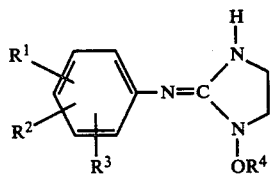

wherein $R^1$, $R^2$ and $R^3$, independently, are hydrogen, alkyl, alkoxy, alkylthio, halogen, trifluoromethyl, cyano or hydroxy and $R^4$ is hydrogen, alkyl, cycloalkyl, cycloalkenyl, alkenyl, alkynyl, carboxyalkyl, carboxyalkenyl, hydroxyalkyl, cyanoalkyl, phenylalkyl, chlorophenylalkyl, tolylalkyl, alkylthioalkyl, alkoxycarbonylalkyl, alkoxyalkoxyalkyl, aminocarbonylalkyl, monoalkylaminocarbonylalkyl, dialkyl-aminocarbonylalkyl, alkoxycarbonylalkenyl, alkoxyalkyl, aminoalkyl, alkylaminoalkyl, dialkylaminoalkyl, phenyl, chlorophenyl, tolyl, (2,2,8-trimethyl-4H-m-dioxino[4,5-c]-pyridin-5-yl)methyl, α-carboxybenzyl, α-alkoxycarbonyl-α-alkylphenyl, or an aromatic heterocyclic residue selected from the group consisting of thienyl, furyl, thiazolyl, oxazolyl, pyrazolyl, imidazolyl, isoxazolyl and isothiazolyl, which is bonded via a —CH($R^5$)— group and is optionally substituted by alkyl or COOR, wherein $R^5$ is hydrogen, methyl, ethyl or n-propyl and R is hydrogen or alkyl, and wherein above, each occurrence, the alkyl, alkoxy and alkylthio groups, independently, are of 1–6 carbon atoms, or a pharmaceutically acceptable acid addition salt thereof.

25. A method of treating hypertension which comprises administering to a warm-blooded animal requiring such treatment a hypotensively effective amount of a compound of the formula

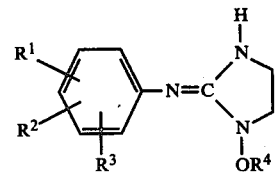

wherein $R^1$, $R^2$ and $R^3$, independently, are hydrogen, alkyl, alkoxy, alkylthio, halogen, trifluoromethyl, cyano or hydroxy and $R^4$ is hydrogen, alkyl, cycloalkyl, cycloalkenyl, alkenyl, alkynyl, carboxyalkyl, carboxyalkenyl, hydroxyalkyl, cyanoalkyl, phenylalkyl, chlorophenylalkyl, tolylalkyl, alkylthioalkyl, alkoxycarbonylalkyl, alkoxyalkoxyalkyl, aminocarbonylalkyl, monoalkylaminocarbonylalkyl, dialkylaminocarbonylalkyl, alkoxycarbonylalkenyl, alkoxyalkyl, aminoalkyl, alkylaminoalkyl, dialkylaminoalkyl, phenyl, chlorophenyl, tolyl, (2,2,8-trimethyl-4H-m-dioxino[4,5-c]-pyridin-5-yl)methyl, α-carboxybenzyl, α-alkoxycarbonyl-α-alkylphenyl, or an aromatic heterocyclic residue selected from the group consisting of thienyl, furyl, thiazolyl, oxazolyl, pyrazolyl, imidazolyl, isoxazolyl and isothiazolyl, which is bonded via a —CH($R^5$)— group and is optionally substituted by alkyl or COOR, wherein $R^5$ is hydrogen, methyl, ethyl or n-propyl and R is hydrogen or alkyl, and wherein above, each occurrence, the alkyl, alkoxy and alkylthio groups, independently, are of 1–6 carbon atoms, or a pharmaceutically acceptable acid addition salt thereof.

* * * * *